United States Patent
Madden et al.

(12) 
(10) Patent No.: US 6,280,934 B1
(45) Date of Patent: Aug. 28, 2001

(54) ASSAY FOR AGENTS WHICH ALTER G-PROTEIN COUPLED RECEPTOR ACTIVITY

(75) Inventors: Kevin T. Madden, Charlestown; Patrick R. Errada, Cambridge; Carlos J. Gimeno, Wellesley, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/078,199

(22) Filed: May 13, 1998

(51) Int. Cl.$^7$ .............................. C12Q 1/68; C12P 19/34; C07H 21/04

(52) U.S. Cl. .......................... 435/6; 435/91.2; 435/254.2; 536/23.1

(58) Field of Search .......................... 435/6, 91.2, 254.2; 536/23.1

(56) References Cited

U.S. PATENT DOCUMENTS

| | | | |
|---|---|---|---|
| 5,482,835 | 1/1996 | King et al. | 435/6 |
| 5,491,084 | * 2/1996 | Chalfie et al. | 435/189 |
| 5,691,188 | 11/1997 | Pausch et al. | 435/254.2 |
| 5,846,819 | 12/1998 | Pausch et al. | 435/320.1 |

FOREIGN PATENT DOCUMENTS

WO 97/11159    3/1997  (WO).

OTHER PUBLICATIONS

Yun et al, "G–Protein coupled receptor from yeast Sacchromyces cerevisiae", Biochem. Biophys. Res. Comm. 240:287–292, 1997.*

Medici, R., et al., "Efficient Signal Transduction by a Chimeric Yeast–Mammalian G Protein α Subunit Gpa1–Gsα Covalently Fused to the Yeast Receptor Ste2", *The EMBO Journal* 16(24):7241–7249 (1997).

Price, L.A., et al., "Functional Coupling of a Mammalian Somatostatin Receptor to the Yeast Pheromone Response Pathway", *Molecular and Cellular Biology*, 15(11):6188–6195 (1995).

Blumer, K.J., et al., "β and γ subunits of a Yeast Guanine Nucleotide–Binding Protein Are Not Essential for Membrane Association of the α Subunit But are Required for Receptor Coupling", *Proc. Natl. Acad. Sci. USA*, 87:4363–4367 (1990).

Nakafuku, M., et al., "Isolation of a Second Yeast *Saccharomyces cerevisiae* Gene (GPA2) Coding for Guanine Nucleotide–Binding Regulatory Protein: Studies on its Structure and Possible Functions", *Proc. Natl. Acad. Sci. USA* 85:1374–1378 (1988).

Papasavvas, S., et al., "Yeast α–Mating Factor Receptor and G–Protein–Linked Adenylyl Cyclase Inhibition Requires RAS2 and GPA2 Activities", *Biochemical and Biophysical Research Communications*, 184(3):1378–1385 (1992).

Manfredi, J.P., et al., "Yeast α Mating Factor Structure–Activity Relationship Derived from Genetically Selected Peptide Agonists and Antagonists of Ste2p", *Molecular and Cellular Biology*, 16(9):4700–4709 (1996).

King, K., et al., "Control of Yeast Mating Signal Transduction by a Mammalian $β_2$–Adrenergic Receptor and $G_s$ α Subunit", *Science* 250:121–123 (1990).

Price, L.A., et al., "Pharmacological Characterization of the Rat $A_{2a}$ Adenosine Receptor Functionally Coupled to the Yeast Pheromone Response Pathway", *Molecular Pharmacology* 50:829–837 (1996).

Conklin, B.R., et al., "Substitution of Three Amino Acids Switches Receptor Specificity of $G_qα$ to that of $G_iα$", *Nature* 363:274–276 (1993).

Kang, Y–S., et al., "Effects of Expression of Mammalian Gα and Hybrid Mammalian–Yeast Gα Proteins on the Yeast Pheromone Response Signal Transduction Pathway", *Molecular and Cellular Biology* 10(6):2582–2590 (1990).

Osawa, S., et al., "$Gα_i$–$Gα_s$ Chimeras Define the Function of α Chain Domains in Control of G Protein Activation and βγ Subunit Complex Interactions", *Cell* 63:697–706 (1990).

Kajkowski, E.M., et al., "Investigation of Growth Hormone Releasing Hormone Receptor Structure and Activity Using Yeast Expression Technologies", *J. of Receptor & Signal Transduction Research*, 17(1–3):293–303 (1997).

Conklin, B.R., et al., "Structural Elements of Gα Subunits that Interact with βγ, Receptors, and Effectors", *Cell* 73:631–641 (1993).

Lorenz, M.C., et al., "Yeast Pseudohyphal Growth I Regulated by GPA2, a G Protein αHomolog", *The EMBO Journal* 16(23):7008–7018 (1997).

Görner, W., et al., "Nuclear Localization of the $C_2H_2$ Zinc Finger Protein Msn2p is Regulated by Stress and Protein Kinase A Activity", *Genetics and Development* 12:586–597 (1998).

Kübler, E, et al., "Gpa2p, a G–protein α–Subunit, Regulates Growth and Pseudohyphal Development in *Saccharomyces cerevisiae* via a cAMP–dependent Mechanism", *The Journal of Biological Chemistry* 272(33):20321–20323 (1997).

Broach, J.R., "RAS Genes in *Saccharomyces cerevisiae*: Signal Tranduction in Search of Pathway", *TIG*7(1):28–32 (1991).

(List continued on next page.)

*Primary Examiner*—Jeffrey Fredman
(74) *Attorney, Agent, or Firm*—Hamilton, Brook, Smith & Reynolds, P.C.

(57) ABSTRACT

The invention relates to a novel transformed yeast cell comprising a first heterologous nucleic acid sequence encoding a G-protein coupled receptor; and second nucleic acid sequence encoding the yeast Gα subunit protein Gpa2; and an optional third heterologous nucleic acid sequence encoding a reporter protein. The G-protein coupled receptor can bind ligand thereby altering the activity of Gpa2 and cellular levels of second messenger molecules and ultimately the activity of target genes. The transformed yeast cell can be used, for example, in in vitro high throughput assays to screen for agonists and antagonists of G-protein coupled receptor ligand activity.

12 Claims, 7 Drawing Sheets

OTHER PUBLICATIONS

Sprague, Jr., G.F., et al., "Pheromone Response and Signal Transduction during the Mating Process of *Saccharomyces cerevisiae*": In, *The Molecular and Cellular Biology of the Yeast Saccharomyces: Gene Expression* Ch. 12 pp. 657–744; Cold Spring Harbor Laboratory Press, 1992.

* cited by examiner

YEAST STRAINS

| Strain Number | Genotype | Background |
|---|---|---|
| MMB1187 | *MATa trp1::hisG leu2::hisG ura3-52* | S1278b |
| MMB1188 | *MATα trp1::hisG leu2::hisG ura3-52* | S1278b |
| MMB1189 | MMB1187 X MMB1188 | S1278b |
| MMB1190 | *MATa trp1::hisG leu2::hisG ura3-52 gpa2D::URA3* | S1278b |
| MMB1191 | *MATa trp1::hisG leu2::hisG ura3-52 gpa2D::hisG* | S1278b |
| MMB1192 | *MATα trp1::hisG leu2::hisG ura3-52 gpa2D::URA3* | S1278b |
| MMB1193 | *MATa trp1::hisG leu2::hisG ura3-52 gpa2D::URA3* / *MATα trp1::hisG leu2::hisG ura3-52 gpa2D::URA3* | S1278b |
| MMB1194 | MMB1193 + pRS414 + pRS415 | S1278b |
| MMB1195 | MMB1193 + pRS414 | S1278b |
| MMB1196 | MMB1193 + PGK-*STE2* | S1278b |
| MMB1197 | *MATa ura3-52 lys2-801 ade2-101 trp1D63 leu2D1* / *MATα ura3-52 lys2-801 ade2-101 trp1D63 leu2D1* | YPH501 |
| MMB1198 | *MATa ura3-52 lys2-801 ade2-101 trp1D63 leu2D1 gpa2D::URA3* | YPH501 |
| MMB1199 | *MATα ura3-52 lys2-801 ade2-101 trp1D63 leu2D1 gpa2D::URA3* | YPH501 |
| MMB1200 | *MATa ura3-52 lys2-801 ade2-101 trp1D63 leu2D1 ras2D::URA3* | YPH501 |
| MMB1201 | *MATα ura3-52 lys2-801 ade2-101 trp1D63 leu2D1 ras2D::URA3* | YPH501 |
| MMB1202 | MMB1190 + pRS415-*GPA2Q300>L* | S1278b |
| MMB1203 | MMB1195 + pRS415-*GPA2Q300>L* | S1278b |
| MMB1204 | MMB1195 + pRS415-*GPA2* | S1278b |
| MMB1205 | MMB1196 + pRS415-*GPA2/GPA1* | S1278b |
| MMB1206 | MMB1196 + pRS415-*GPA2* | S1278b |
| MMB1207 | MMB1196 + pRS415-*GPA2Q300>L* | S1278b |
| MMB1208 | MMB1193 + pRS415 | S1278b |
| MMB1209 | MMB1193 + pRS415-*GPA2/GPA1* + YPGE2 | S1278b |
| MMB1210 | MMB1208 + PGK-*STE2* | S1278b |
| MMB1211 | MMB1208 + PGK-*STE2-GPA2* | S1278b |
| MMB1212 | MMB1208 + PGK-*STE2-GPA2/GPA1* | S1278b |
| MMB1213 | MMB1196 + pRS415-*GPA2Q300>L* | S1278b |
| MMB1274 | MMB1193 + pYPGE2 + pRS415-*GPA2Q300>L* | S1278b |
| MMB1276 | MMB1193 + pYPGE2 + pRS415 | S1278b |

FIGURE 2

NORMALIZED EXPRESSION VALUES

PGK-STE2 + GPA2/GPA1 coupling experiment:

|  | STE2 | GPA2/GPA1 | ACT1 |
|---|---|---|---|
| 3 hour treatment with alpha factor | 4748<br>4748 | 35<br>40 | 4673<br>4720 |
| 6 hour treatment with alpha factor | 3419<br>3419 | 86<br>96 | 3422<br>3423 |

PGK-STE2-GPA2 fusion experiment:

|  | STE2-GPA2 (*) | STE2-GPA2 (*) | ACT1 |
|---|---|---|---|
| + alpha factor | 5916<br>5493 | 10920<br>11014 | 2968<br>2989 |
| - alpha factor | 2924<br>2902 | 18459<br>18308 | 2226<br>2513 |
| * underline denotes hybridization for specific portion of the fusion | | | |

FIGURE 3

| Clone | A | B | C | D | E | F | G | H | I |
|---|---|---|---|---|---|---|---|---|---|
| YMR323W | 0.0281 | 3.2290 | 0.1327 | 0.1538 | 0.0310 | 0.0411 | 0.1461 | 4.7199 | 0.9080 |
| YMR323W | 0.0341 | 3.2208 | 0.1493 | 0.1804 | 0.0450 | 0.0463 | 0.1971 | 4.3764 | 0.7574 |
| YBL100C | 0.0494 | 1.000 | 0.0297 | 0.0970 | 0.0084 | 0.0297 | 0.0051 | 0.6006 | 5.8498 |
| YBL100C | 0.0895 | 1.7337 | 0.0506 | 0.1607 | 0.0160 | 0.0292 | 0.0091 | 0.5654 | 5.5762 |
| YDR187C | 0.0547 | 0.8800 | 0.1443 | 0.1324 | 0.0295 | 0.1640 | 0.0778 | 2.6368 | 1.8550 |
| YDR187C | 0.0603 | 0.7159 | 0.1472 | 0.1320 | 0.0327 | 0.2056 | 0.0798 | 2.4407 | 1.8452 |
| YEL045C | 0.0631 | 1.2552 | 0.3193 | 0.2550 | 0.0259 | 0.2544 | 0.1310 | 5.0636 | 2.4370 |
| YEL045C | 0.0980 | 1.3303 | 0.3080 | 0.1801 | 0.0434 | 0.2315 | 0.1363 | 3.1418 | 2.2593 |
| YBL096C | 0.0616 | 1.3051 | 0.2273 | 0.3903 | 0.0730 | 0.1741 | 0.2692 | 3.6900 | 0.8441 |
| YBL096C | 0.0645 | 0.9061 | 0.2251 | 0.2755 | 0.0549 | 0.2484 | 0.1915 | 3.4889 | 1.1755 |
| YNL028W | 0.0673 | 2.4977 | 0.1682 | 0.0819 | 0.2440 | 0.0673 | 0.6094 | 2.4977 | 0.2761 |
| YNL028W | 0.0744 | 1.8099 | 0.1346 | 0.0805 | 0.1653 | 0.0744 | 0.2992 | 1.8099 | 0.4498 |
| YFR056C | 0.0819 | 0.8314 | 0.2294 | 0.1231 | 0.1017 | 0.2759 | 0.2849 | 2.8017 | 0.8052 |
| YFR056C | 0.0834 | 0.9438 | 0.3018 | 0.2775 | 0.0754 | 0.3198 | 0.2727 | 3.6170 | 1.1068 |
| YFR034C (PHO4) | 0.0850 | 0.8223 | 0.1759 | 0.2612 | 0.1135 | 0.2139 | 0.2350 | 2.0701 | 0.7483 |
| YFR034C (PHO4) | 0.1023 | 0.7858 | 0.1458 | 0.2516 | 0.1265 | 0.1855 | 0.1803 | 1.4254 | 0.8089 |
| YCL046W | 0.1111 | 2.9164 | 0.3240 | 0.1294 | 0.0510 | 0.1111 | 0.1488 | 2.9164 | 2.1767 |
| YCL046W | 0.2291 | 2.2406 | 0.3354 | 0.2416 | 0.0850 | 0.1497 | 0.1244 | 1.4637 | 2.6966 |
| YCLX09W | 0.1508 | 1.6245 | 0.3924 | 0.1664 | 0.0436 | 0.2416 | 0.1135 | 2.6019 | 3.4559 |
| YCLX09W | 0.4284 | 0.5885 | 0.3424 | 0.3808 | 0.1048 | 0.5818 | 0.0837 | 0.7993 | 4.0888 |
| YPL281C | 0.1957 | 1.0501 | 0.4327 | 0.1607 | 0.1207 | 0.4120 | 0.2669 | 2.2114 | 1.6211 |
| YPL281C | 0.2130 | 0.9735 | 0.3813 | 0.1350 | 0.1422 | 0.3917 | 0.2546 | 1.7905 | 1.4974 |
| YJL045W | 0.2298 | 1.2109 | 0.1637 | 0.3494 | 0.1760 | 0.1352 | 0.1254 | 0.7125 | 1.3055 |
| YJL045W | 0.2612 | 0.9373 | 0.1212 | 0.3880 | 0.2136 | 0.1293 | 0.0991 | 0.4640 | 1.2226 |
| YGL046W | 0.2495 | 0.5298 | 0.2095 | 0.1307 | 0.1923 | 0.3955 | 0.1615 | 0.8398 | 1.2976 |
| YGL046W | 0.2580 | 0.6407 | 0.2301 | 0.1675 | 0.1710 | 0.3592 | 0.1525 | 0.8918 | 1.5090 |
| YCL040W (GLK1) | 0.2562 | 1.0091 | 0.1946 | 0.3210 | 0.2658 | 0.1928 | 0.2019 | 0.7596 | 0.9636 |
| YCL040W (GLK1) | 0.2780 | 0.8214 | 0.1813 | 0.3368 | 0.3184 | 0.2207 | 0.2076 | 0.6521 | 0.8732 |
| YML058C-A | 0.1143 | 0.9900 | 0.2614 | 0.1609 | 0.1000 | 0.2641 | 0.2286 | 2.2866 | 1.1437 |
| YML058C-A | 0.2583 | 1.4008 | 0.3751 | 0.2228 | 0.2242 | 0.2678 | 0.3256 | 1.4521 | 1.1520 |
| YJR114W | 0.2763 | 1.0503 | 0.2835 | 0.3106 | 0.3325 | 0.2699 | 0.3412 | 1.0262 | 0.8309 |
| YJR114W | 0.2827 | 0.8228 | 0.2560 | 0.3530 | 0.3104 | 0.3111 | 0.2810 | 0.9053 | 0.9109 |
| YOR135C (IDH2) | 0.3016 | 1.1667 | 0.3510 | 0.3321 | 0.3417 | 0.3008 | 0.3976 | 1.1638 | 0.8826 |
| YOR135C (IDH2) | 0.3717 | 1.2960 | 0.3779 | 0.4975 | 0.3795 | 0.2916 | 0.3858 | 1.0167 | 0.9794 |
| YML035C-A | 0.1970 | 1.0000 | 0.1673 | 0.4604 | 0.1883 | 0.1673 | 0.1599 | 0.8492 | 1.0466 |
| YML035C-A | 0.3635 | 1.0000 | 0.2747 | 0.3951 | 0.2183 | 0.2747 | 0.1649 | 0.7556 | 1.6652 |
| YFL014W (HSP12) | 0.5092 | 0.3496 | 0.0418 | 3.0850 | 0.4622 | 0.1196 | 0.0380 | 0.0821 | 1.1016 |

FIGURE 4A

| Clone | A | B | C | D | E | F | G | H | I |
|---|---|---|---|---|---|---|---|---|---|
| YBR072W (HSP26) | 0.5840 | 0.3008 | 0.0346 | 1.8588 | 0.3680 | 0.1149 | 0.0218 | 0.0592 | 1.5870 |
| YBR072W (HSP26) | 0.6414 | 0.2626 | 0.0366 | 1.7013 | 0.4838 | 0.1393 | 0.0276 | 0.0570 | 1.3258 |
| YNL134C | 0.6965 | 0.6071 | 0.3132 | 0.8143 | 0.8414 | 0.5159 | 0.3783 | 0.4497 | 0.8279 |
| YNL134C | 0.5230 | 0.5493 | 0.3586 | 0.9623 | 0.4883 | 0.6529 | 0.3348 | 0.6857 | 1.0710 |
| YML128C | 0.6526 | 0.6221 | 0.1051 | 0.8975 | 0.7583 | 0.1689 | 0.1221 | 0.1610 | 0.8606 |
| YML128C | 0.6382 | 0.6166 | 0.0909 | 0.6952 | 0.8724 | 0.1475 | 0.1243 | 0.1425 | 0.7315 |

FIGURE 4B

| Experiment 1 | | | | | |
|---|---|---|---|---|---|
| Clone | activated/Δ | activated/Δ | activated/Δ | activated/Δ | low nitrogen |
|  | (low nitrogen) | (low nitrogen) | (rich media) | (rich media) | rich media |
| YFL014W (HSP12) | 0.0652 | 0.3150 | 0.2188 | 0.3011 | 14.0437 |
| YFL014W (HSP12) | 0.0443 | 0.2224 | 0.2088 | 0.3946 | 20.0044 |
| YBR072W (HSP26) | 0.0344 | 0.3161 | 1.0000 | 1.0000 | 7.0346 |
| YBR072W (HSP26) | 0.0336 | 0.2906 | 1.0000 | 1.0000 | 7.7029 |
| YNL134C | 0.3373 | 0.2238 | 0.4665 | 0.5052 | 6.0718 |
| YNL134C | 0.3351 | 0.2592 | 0.4379 | 0.4794 | 5.9897 |
| YML128C | 0.1532 | 0.2822 | 0.4432 | 0.7811 | 16.6043 |
| YML128C | 0.1538 | 0.3098 | 0.4946 | 0.6999 | 15.0432 |
|  |  |  |  |  |  |
| Experiment 2 |  |  |  |  |  |
| Clone | activated/Δ | activated/Δ | activated/Δ | activated/Δ |  |
| YFL014W | 0.1114 | 0.1589 | 0.1323 | 0.1887 |  |
| YBR072W (HSP26) | 0.1540 | 0.1926 | 0.1807 | 0.2260 |  |
| YNL134C | 0.8018 | 0.3309 | 0.9233 | 0.3810 |  |
| YML128C | 0.7952 | 0.3667 | 0.8818 | 0.4067 |  |
|  |  |  |  |  |  |
| Experiment 3 |  |  |  |  |  |
| Clone | activated/Δ | activated/Δ |  |  |  |
| YFL014W (HSP12) | 0.3605 | 0.9309 |  |  |  |
| YBR072W (HSP26) | 0.1230 | 0.1478 |  |  |  |
| YNL134C | 0.5190 | 0.2137 |  |  |  |
| YML128C | 0.4371 | 0.2802 |  |  |  |
|  |  |  |  |  |  |
| Experiment 4 |  |  |  |  |  |
| Clone | activated/Δ |  |  |  |  |
| YFL014W (HSP12) | 0.0418 |  |  |  |  |
| YFL014W (HSP12) | 0.0495 |  |  |  |  |
| YBR072W (HSP26) | 0.0346 |  |  |  |  |
| YBR072W (HSP26) | 0.0366 |  |  |  |  |
| YNL134C | 0.3132 |  |  |  |  |
| YNL134C | 0.3586 |  |  |  |  |
| YML128C | 0.1051 |  |  |  |  |
| YML128C | 0.0909 |  |  |  |  |

FIGURE 5

| CLONE | Number of STRE(s) |
|---|---|
| YMR323w | 2 |
| YBL100c | 0 |
| YDR187c | 0 |
| YEL045c | 2 |
| YBL096c | 1 |
| YNL028w | 0 |
| YFR056c | 0 |
| PHO4 | 2 |
| YCL046w | 2 |
| YCLX09w | 0 |
| YPL281c | 2 |
| YJL045w | 0 |
| YGL046w | 2 |
| GLK1 | 4 |
| YML058c-a | 2 |
| YJR114w | 1 |
| IDH2 | 2 |
| YML035c-a | 0 |
| HSP12 | 7 |
| HSP26 | 4 |
| YNL134c | 2 |
| YML128c | 2 |

FIGURE 6

ASSAY FOR AGENTS WHICH ALTER G-PROTEIN COUPLED RECEPTOR ACTIVITY

BACKGROUND OF THE INVENTION

Communication between cells is essential to the maintenance of homeostasis of an organism. Extracellular signaling molecules, such as hormones and neurotransmitters, mediate cell-cell communication by acting through specific receptors located on the plasma membrane and in the cytoplasm of target cells.

G-protein coupled receptors are a class of seven-transmembrane domain polypeptides which transduce an extracellular signal into a cellular response. Following binding of a ligand to a G-protein coupled cell surface receptor, the G-protein coupled receptor activates an intracellular guanine nucleotide-binding protein, a G-protein, which mediates a cellular response to the extracellular signaling molecule (FIG. 1).

G-proteins are heterotrimeric polypeptides composed of α, β- and γ-subunits. Upon binding of ligand, the G-protein coupled receptor activates the G-protein by promoting the exchange of bound GDP for GTP in the α-subunit and dissociation of the activated α-subunit from βγ-subunits (Lewin, B., "Signal Transduction", *Genes VI*, Oxford University Press, New York, pp. 1053–1087 (1997)). The GTP-bound Gα subunit and the liberated αγ dimeric subunit alter the activity of effectors in the target cell, for example, by altering the activity of adenylate cyclase and hence the levels of the second messenger cAMP, thereby altering the transcriptional activity of cAMP dependent genes.

G-proteins and G-protein-mediated cell signaling systems are highly conserved among eukaryotes from such diverse species as mammals, including humans, to yeast. (See, for example, Stryer, L. et al., *Ann. Rev. Cell Biol.* 2:391 (1986) and Lewin, B., "Signal Transduction", *Genes VI*, Oxford University Press, New York, pp. 1053–1087 (1997)). Thus, due to the ease of experimental manipulation, it has been recognized that yeast can serve as a useful model for studying and evaluating G-protein coupled receptors and their ligands, as well as agents which act as antagonists and agonists of ligand activity in eukaryotic cells, including mammalian cells.

In the widely used yeast strain, *Saccharomyces cerevisiae*, two distinct G-protein a-subunit proteins, Gpa1 and Gpa2, have been described (Miyajima, I., et al., *Cell*, 50:1011–1019 (1987); Nakafuku, M., et al., *Proc. Natl. Acad. Sci. U.S.A.* 85:1374–1378 (1988); Kübler, E., et al.,*J. Biol. Chem.* 272:20321–20323 (1997)). Gpa1, also known as Scg1, is an α-subunit of the heterotrimeric G-protein, which regulates a mitogen-activated protein kinase pathway that is required for the yeast response to mating pheromone. Gpa2 is the α-subunit of a G-protein which is involved in pseudohyphal growth, and this G-protein functions by stimulating the yeast cAMP-response. The only known β- and γ-subunits in yeast are Ste4 and Ste18, respectively (Whiteway, M., et al., *Cell* 56:467–477 (1989)).

To date, there have been reports of the use of Gpa1, the α-subunit of a G-protein required to inhibit the pheromone response, with yeast and mammalian G-protein cell surface receptors, a process which results in Gpa1 activation upon ligand stimulation. For example, Gpa1 has been functionally linked to the rat $A_{2a}$ adenosine or human β2-adrenergic G-protein coupled receptor, resulting in adenosine agonist-dependent growth elicited by activation of the yeast pheromone-responsive pathway (Price, L. A., et al., *Molec. Pharmacol.* 50:829–837 (1996); Pausch, M. H., et al., U.S. Pat. No. 5,691,188 (1997)). Gpa1 has also been used with the rat somatostatin G-protein coupled receptor, resulting in growth-promoting signaling through pheromone-responsive pathways (Price, L. A., et al., *Molec. Cell Biol.* 15:6188–6195 (1995); Pausch, M. H., et al., U.S. Pat. No. 5,691,188 (1997)). Chimeric Gpa1-mammalian Gα subunit proteins (Kang, Y.-S., et al., *Molec. Cell Biol.* 10:2582–2590 (1990); Price, L. A., et al., *Molec. Cell Biol.* 15:6188–6195 (1995); Medici, R., et al., *EMBO J.* 16:7241–7249 (1997)) and chimeric mammalian-yeast cell surface receptors (Pausch, M. H., et al., U.S. Pat. No. 5,691,188 (1997)) which bind ligands, have also been described. Mammalian G-protein coupled receptors have been functionally linked to mammalian Gα subunits through pheromone dependent pathways in yeast host cells lacking the endogenous GPA1 gene (King, K., et al., U.S. Pat. No. 5,482,835 (1996)).

These approaches require several genetic modifications of a typical laboratory yeast strain in order to effectively monitor the effects of extracellular signaling molecules, such as additional mutations in the FAR1 or SST2 genes. The existing technologies necessitate activation of the signal transduction pathway attributed to the α-subunit of the yeast G-protein, Gpa1, and are limited to evaluation based on pheromone-responsive mating criteria. Moreover, previous work has been limited to G-protein coupled receptors and Gα proteins which are normal cognate pairs (e.g., cell surface receptors and G-proteins which are able to associate and mediate effector pathways by G-protein activation). Additionally, these approaches often require deletion of the endogenous yeast Gα protein.

Thus, there is a continued need to develop new and improved methods for assessing agents which have agonistic and antagonistic effects on specific G-protein coupled receptors.

SUMMARY OF INVENTION

Work described herein shows that yeast cells transformed with a nucleic acid construct comprising a promoter operably linked to a first heterologous nucleic acid sequence encoding a G-protein coupled receptor which is operably linked to a second nucleic acid sequence encoding a Gα protein which is not a cognate protein of the mammalian G-protein coupled receptor, can be used to assess G-protein mediated signal transduction pathways. Expression of the first and second nucleic acid sequences produces a fusion protein in which the Gα protein is linked to the mammalian G-protein coupled receptor. Binding of a ligand to the mammalian G-protein coupled receptor activates the Gα protein, which in turn mediates a cellular response to the extracellular signal, such as regulation of specific effectors including adenylate cyclase and cyclic adenosine monophosphate (cAMP). In a particular embodiment the Gα protein is a yeast Gα protein, and in a particularly preferred embodiment the yeast Gα protein is Gpa2.

Thus, the invention relates to a transformed yeast cell comprising a nucleic acid construct comprising a promoter operably linked to a first heterologous nucleic acid sequence which is operably linked to a second nucleic acid sequence, wherein said first heterologous nucleic acid sequence encodes a mammalian G-protein coupled receptor, and wherein said second nucleic acid sequence encodes a Gα protein which is not a cognate protein of said G-protein coupled receptor, such that expression of the first and second DNA sequences produces a fusion protein wherein the Gα protein is linked to the mammalian G-protein coupled receptor. In one embodiment, binding of a ligand to the mammalian G-protein coupled receptor results in alteration of cellular levels or activity of an effector molecule (e.g., adenylate cyclase) or a second messenger (e.g., cAMP) or combinations thereof. In a preferred embodiment, the promoter is functional in yeast. In one embodiment, the Gα protein is a yeast Gα protein. In a preferred embodiment, the yeast Gα protein is Gpa2.

The invention also relates to a transformed yeast cell comprising a DNA construct comprising a promoter operably linked to a first nucleic acid sequence which is operably linked to a second nucleic acid sequence, wherein the first nucleic acid sequence encodes a G-protein coupled receptor, and wherein the second nucleic acid sequence encodes a yeast Gpa2 protein, such that expression of the first and second nucleic acid sequences produces a fusion protein wherein the yeast Gpa2 protein is linked to the G-protein coupled receptor. In a particular embodiment, the G-protein coupled receptor is STE2. In one embodiment, the transformed yeast cell is a diploid cell.

In one embodiment of the invention, the promoter is a constitutive promoter. In another embodiment, the endogenous yeast gene encoding Gpa2 has a loss of function mutation. In particular embodiments, the mammalian G-protein coupled receptor is selected from the group consisting of somatostatin and MC4. In one embodiment the Gα protein is linked to the cytoplasmic domain of the mammalian G-protein coupled receptor. In another embodiment, there is a loss of function mutation in the endogenous yeast genes encoding STE4, STE18 or both STE4 and STE18.

In another embodiment of the invention, the transformed yeast cell further comprises a nucleic acid construct comprising a Gpa2-responsive promoter operably linked to a third nucleic acid sequence encoding a reporter gene. In a particular embodiment, the Gpa2-responsive promoter (e.g., a cAMP-responsive promoter) is a promoter of a gene selected from the group consisting of YMR323w, YBL100c, YDR187c, YEL045c, YBLO96c, YNL028w, YFR056c, PHO4, YCL046w, YCLX09w, YPL281c, YJL045w, YGL046w, GLK1, YML058c-a, YJR114w, IDH2, YML035c-a, HSP12, HSP26, YNL134c and YML128c. In one embodiment, the reporter gene is selected from the group consisting of enzymes such as β-galactosidase, β-glucoronidase, β-glucosidase, acid phosphatase, invertase; luminescent molecules such as green fluorescent protein and firefly luciferase; and auxotrophic markers such as HIS3, URA3 and LYS2.

The invention further relates to a nucleic acid construct comprising a promoter operably linked to a first heterologous nucleic acid sequence which is operably linked to a second nucleic acid sequence, wherein said first heterologous nucleic acid sequence encodes a mammalian G-protein coupled receptor, and wherein the second nucleic acid sequence encodes a Gα protein which is not a cognate protein of said mammalian G-protein coupled receptor, such that expression of the first and second nucleic acid sequences produces a fusion protein wherein the Gα protein is linked to the mammalian G-protein coupled receptor. In a preferred embodiment, the promoter is functional in yeast. In one embodiment, the Gα protein is a yeast Gα protein. In a preferred embodiment, the yeast Gα protein is Gpa2. In one embodiment of the invention, the promoter is a constitutive promoter.

The invention further provides a method of identifying agents which alter G-protein coupled receptor function, comprising providing a transformed yeast cell of the present invention, contacting the yeast cell with an agent to be tested; and detecting the level of an effector or a second messenger associated with G-protein coupled receptor function. In a preferred embodiment, the Gα protein is a yeast Gα protein, and in a particularly preferred embodiment the yeast Gα protein is Gpa2. In a particular embodiment the effector is adenylate cyclase, guanylate cyclase, phospholipase C-β, or any combination thereof. In a particular embodiment, the second messenger is cAMP, cGMP, diacylglycerol, inositol triphosphate, calcium or any combination thereof. In one embodiment, the agent to be tested is present along with a ligand of the G-protein coupled receptor, and thus, the step of contacting the yeast cell with the agent to be tested is carried out in the presence of the ligand. In one embodiment, the agent is an agonist; in another embodiment, the agent is an antagonist. In a preferred embodiment, the transformed yeast cell further comprises a nucleic acid construct comprising a Gpa2-responsive promoter operably linked to a third nucleic acid sequence encoding a reporter gene, and the step of detecting is carried out by monitoring the expression of said reporter gene.

The invention also relates to a method of identifying genes which are responsive to G-protein coupled receptor activation of a yeast Gα protein and resultant effector or second messenger activation, comprising providing a transformed yeast cell of the invention, contacting the cell with a ligand of the G-protein coupled receptor, and detecting alteration of gene expression relative to the same yeast cell which has not been contacted with the ligand. In another embodiment, the changes in gene expression elicited by the addition of ligand to a cell containing a G-protein coupled receptor can also be compared to the transcriptional changes elicited by the expression of a constitutively active allele of the α-subunit of a G-protein relative to a cell containing the wildtype or loss of function α-subunit of a G-protein. In a particular embodiment, the Gα protein is Gpa2.

The inventions which are described herein provide alternative and improved mechanisms for screening for ligands for G-protein coupled receptors, as well as agonists and antagonists of ligand receptor interactions. In contrast to previous work, the present invention does not require additional genetic mutations in the transformed yeast cell, for example in the FAR1, FUS3 or FUS1 genes, in order to detect the response of the cell to the receptor-dependent activation of G-protein coupled receptors. Nor does it require mutations in genes encoding downstream elements of G-protein signal transduction pathways to increase the sensitivity of detection, for example a mutation in the SST2 gene to augment pheromone responsive pathways. Moreover, the invention thereby offers greater opportunities for high throughput screening of potential mediators of mammalian G-protein activation than previously available.

BRIEF DESCRIPTION OF THE FIGURES

FIG. 2 is a list of transformed yeast cell strains by number, genotype and background.

FIG. 3 depicts the expression data from transcriptional profiling experiments in which STE2 was expressed as a fusion protein with a GPA2/GPA1 chimeric protein using the constitutively active PGK promoter (PGK-STE2+GPA2/GPA1) and as a fusion protein with GPA2 using the constitutively active PGK promoter (PGK-STE2-GPA2). Actin (ACT1) expression was also determined.

FIGS. 4A and 4B depict the expression data from transcriptional profiling experiments using transformed yeast cells (clones). The following ratios of transformed yeast cells were used to compare transcriptional profiles:

Figure 1:
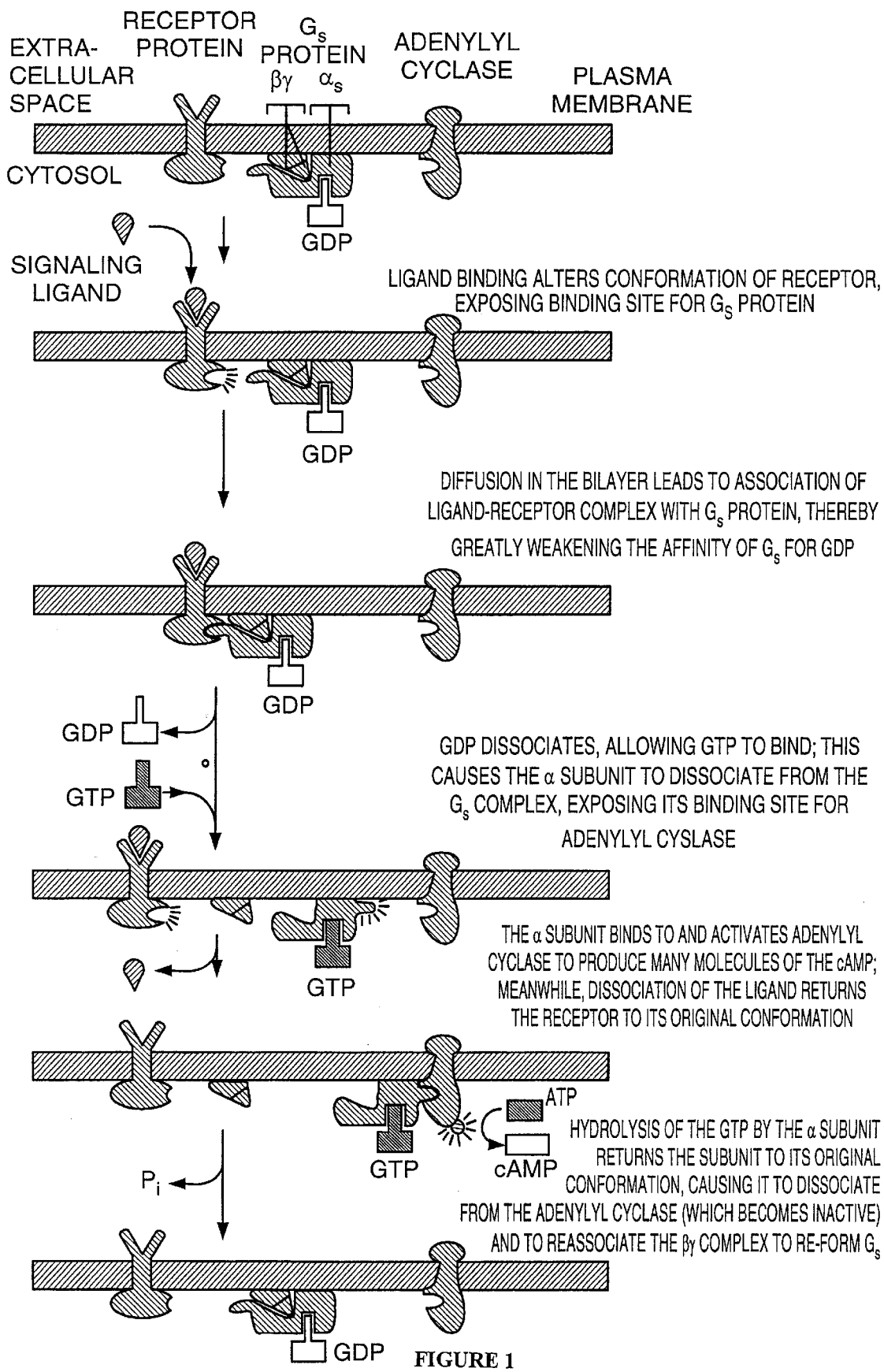
FIG. 1 schematically illustrates a model of ligand binding to a G-protein coupled cell surface receptor and G-protein activation. The figure is from page 739 of Alberts, B. et al., "Molecular Biology of the Cell", third edition, Garland Publishing, Inc., New York, N.Y. (1994).

(A) PGK-STE2-GPA2+α factor/PGK-STE2-GPA2
(B) GPA2 Q300>L+α factor/GPA2 Q300>L
(C) GPA2 Q300>L +α factor/PGK-STE2-GPA2
(D) PGK-STE2-GPA2/GPA1+α factor/PGK-STE2-GPA2
(E) PGK-STE2-GPA2+α factor/PGK-STE2+α factor
(F) GPA2 Q300>L/PGK-STE2-GPA2
(G) GPA2 Q300>L+α factor/PGK-STE2+α factor
(H) GPA2 Q300>L+α factor/PGK-STE2-GPA2+a factor
(I) PGK-STE2+α factor/PGK-STE2-GPA2

FIG. 5 depicts the expression data from transcriptional profiling experiments using transformed yeast cells (clones) that have been deleted for the GPA2 gene and contain either plasmid GPA2 Q300>L (activated) or vector pRS415 (Δ). The ratio of transcriptional profiles from clones expressing GPA2 Q300>L (activated) to clones containing vector pRS415 (Δ) were calculated for experiments performed in both rich (synthetic complete) (Experiments 1, 2, 3 and 4) or low nitrogen (SLAD) (Experiment 1) media.

FIG. 6 depicts an analysis of upstream regulatory sequence from genes which were identified by transcriptional profiling to be repressed by the activation of Gpa2 signaling. Upstream regulatory sequence of 750 base pairs in length was search for the core sequence of a yeast STRE (5'-CCCCT-3' or complimentary 5'-AGGGG-3').

DETAILED DESCRIPTION OF THE INVENTION

As set forth above, the present invention relates to the discovery that mammalian G-protein coupled cell surface receptors can be functionally linked (e.g., in a fusion protein) to the α-subunit of a non-cognate G-protein in yeast cells. As used herein "functionally linked" is intended to include linkage of a G-protein coupled receptor to a Gα subunit of a G-protein, such as by a fusion protein, by use of a chimeric protein which allows interaction and signal transduction, or by linking the G-protein coupled receptor and Gα subunit to other molecules which are known to interact. Functional linkage results in association of the G-protein coupled receptor and Gα and mediates an intracellular response. The G-protein coupled receptor is activated by ligand binding and induces activation of the Gα subunit, e.g., from a G-protein such as Gpa2, resulting in phenotypic (such as pseudohyphal growth) and molecular (such as transcription of Gpa2-responsive genes) changes in the cells. In one embodiment, the G-protein coupled receptor is physically coupled to the G-protein α-subunit in a fusion protein. The invention also encompasses the use of transformed yeast cells of the invention in cellular screens for identifying ligands of the G-protein coupled receptors or agents which mimic, enhance or inhibit native ligand-receptor binding or function. Another aspect of the invention also encompasses a method of identifying genes which are responsive to G-protein coupled receptor activation of Gpa2 and effector molecules or second messengers produced by Gpa2 activation. The invention also pertains to nucleic acid constructs encoding the fusion proteins and to the fusion proteins produced by expression of such nucleic acid constructs. Another embodiment of the invention includes the use of α-subunits of G-proteins which are linked to G-protein coupled receptors without the generation of a fusion protein.

The term "mammalian", as defined herein, refers to any vertebrate animal, including monotremes, marsupials and placental, that suckle their young and either give birth to living young (eutharian or placental mammals) or are egg-laying (metatharian or nonplacental mammals). Examples of mammalian species include primates (e.g., humans, monkeys, chimpanzees, baboons), rodents (e.g., rats, mice, guinea pigs, hamsters) and ruminants (e.g., cows, horses).

The term "transformed yeast cell" as used herein is a yeast cell which has been transformed with vectors constructed using recombinant DNA technologies and which expresses the protein encoded by the nucleic acid constructs contained in the vector. The yeast cell can be preferably *Saccharomyces cerevisiae,* and additionally or alternatively, for example, *Kluveromyces lactis* (U.S. Pat. No. 4,806,472) or *Pichia pastoris* (U.S. Pat. No. 4,855,231). "Transformed" refers to the acquisition of new or altered genetic features by incorporation of additional nucleic acids, e.g., DNA. "Expression" of the genetic information of a transformed yeast cell is a term of art which refers to the directed transcription of DNA to generate RNA which is translated into a polypeptide.

Nucleic acid constructs are defined herein as heteropolymers of nucleic acid molecules. Nucleic acid molecules are meant to refer to chains of nucleotides joined together by phosphodiester bonds to form nucleic acid sequences. As used herein the term "nucleic acid" is an equivalent of the term "nucleotide" and the term "molecule" is an equivalent of the term "sequence"; therefore, for example, a nucleotide sequence is equivalent to a nucleic acid molecule. The nucleic acid molecules can be double stranded or single stranded and can be deoxyribonucleotide (DNA) molecules, such as cDNA or genomic DNA, or ribonucleotide (RNA) molecules. As such, the nucleic acid molecule can include one or more coding sequences. The term "coding sequence", as used herein, is a segment or region of a gene which is represented in the mature mRNA transcription product and is translated into protein. By way of illustration, the yeast vectors used in the invention can contain an origin of replication from the yeast two micron plasmid or an autonomously replicating sequence (ARS). In one example, the nucleic acid molecule contains a single open reading frame which encodes the mammalian G-protein coupled receptor or the α-subunit of a G-protein. Alternatively, a nucleic acid construct can contain a nucleic acid sequence comprising two coding sequences which are linked. Such a multi-coding sequence construct can comprise a coding sequence for a G-protein coupled receptor operably linked to a coding sequence for the α-subunit of a G-protein, a transcriptional termination sequence, and optionally a yeast promoter operably linked to a reporter gene useful for monitoring expression of the fusion protein. Examples of widely-used reporter molecules include enzymes such as β-galactosidase, β-glucoronidase, β-glucosidase, acid phosphatase and invertase; luminescent molecules such as green fluorescent protein and firefly luciferase; and auxotrophic markers such as HIS3, URA3 and LYS2 (see, for example, Chapter 9 in Ausubel, F. M., et al. "Current Protocols in Molecular Biology", John Wiley & Sons, Inc., (1998)). The generation of nucleic acid constructs and detection of reporter genes are standard molecular biological procedures and well known in the art, and thus alternative combinations or modifications of the reporter elements according to the present invention would be apparent to the person of skill in the art.

Thus, the nucleic acid molecules of the invention can include sequences which encode mammalian G-protein coupled receptors and G-protein subunits, as well as one or more of the following optional sequences, in a functional relationship: regulatory sequences, an origin of replication, splice donor sites, splice acceptor sites, introns, transcription termination sequences, 5' and 3' untranslated regions, polyadenylation sequences, negative and/or positive selective markers, and replication sequences.

The nucleic acid molecules preferably comprise regulatory sequences. Regulatory sequences are art-recognized and include cis-acting elements that control transcription and regulation, such as promoter sequences, enhancers, ribosomal binding sites, and transcription binding sites. Selection of the promoter will generally depend upon the nucleic acid construct and desired expression properties. In a preferred embodiment, promoter sequences are selected which are functional in yeast. Examples of suitable promoters for use in yeast vectors include 3-phosphoglycerate kinase (Hitzeman et al., *J. Biol. Chem.* 255:2073 (1980), metallothionein, enolase, glyceraldehyde-3-phosphate dehydrogenase, hexokinase, pyruvate decarboxylase, phosohofructokinase, glucose-6-phosphate isomerase, 3-phosphoglycerate mutase, pyruvate kinase, triosephosphate isomerase, phosphoglucose isomerase and glucokinase promoters (Hess, et al., *J. Adv. Enzyme Reg.* 7:149 (1968); Holland, et al., *Biochemistry* 17:4900 (1978)) and are described in detail in art-recognized technical laboratory texts including Ausubel, F. M. et al., "*Current Protocols in Molecular Biology*", John Wiley & Sons, Inc. (1998).

The nucleotides which comprise the nucleic acid molecule can be isolated from nature, modified from native sequences or manufactured de novo, as described, for example, in Ausubel, F. M., et al., "*Current Protocols in Molecular Biology*", John Wiley & Sons (1998) and Sambrook, et al., "*Molecular Cloning: A Laboratory Manual*", Second Edition (1989). The nucleotides can then be isolated and fused together by methods known in the art, such as by exploiting and manufacturing compatible cloning or restriction sites.

The nucleic acid molecules of the invention described herein comprise nucleic acids having sequences identical to sequences of naturally occurring genes, including polymorphic or allelic variants, and portions (fragments) thereof, or variants of the naturally occurring genes. Such variants include mutants differing by the addition, deletion or substitution of one or more residues, modified nucleic acids in which one or more residues are modified (e.g., DNA or RNA analogs), and mutants comprising one or more modified residues.

The coding regions of the nucleic acid molecule code for a mammalian G-protein coupled receptor and a Gα subunit and, optionally, a reporter gene. Where the G-protein coupled receptor and Gα subunit are the wild-type cellular surface receptor and G-protein, respectively, or a binding fragment thereof, the nucleic acid molecule coding regions can correspond to the wild-type sequences which encode the receptor. Alternatively, because some amino acids are encoded by a plurality of different codons, the nucleotide coding sequence can be altered to produce a codon encoding the same amino acid as the native codon (e.g., a silent mutation). This can be advantageous where a codon is preferred by a selected yeast cell.

Where the G-protein subunit or cell surface receptor is a mutant or variant of a native sequence, generally, the nucleic acid sequence will be mutated correspondingly. The mutations to the nucleic acid sequence can be conserved or nonconserved. The phrase "conserved substitution" is intended to mean a nucleic acid sequence mutation which encodes an amino acid which possesses similar side chains and properties (e.g., hydrophilic, hydrophobic, aromatic) as the amino acid encoded by the non-mutated nucleic acid sequence. It is preferred, e.g., for ease of manufacture of the nucleic acid sequence, to maintain as much of the native sequence as possible. As used herein, percent identity is determined using a Basic Local Alignment Search Tool (BLAST) (Altschul, S. F., et al., *Proc. Natl. Acad. Sci. U.S.A.* 85:2444–2448 (1988)) comparison protocol. In one embodiment, the BLAST parameters are set such that they yield a sequence having at least about 75% sequence identity with the corresponding native nucleotide sequence, preferably, at least about 80% sequence. In a more preferred embodiment, the percent sequence identity is at least about 85%, and still more preferably, at least about 95%.

The nucleic acid molecules can be inserted into a construct which can, optionally, replicate and/or integrate into the yeast cell, by known methods. A number of yeast cell cultures and expression vectors for transforming yeast cells are known (see, for example, U.S. Pat. Nos. 4,745,057; 4,797,359; 4,615,974; 4,880,734; 4,711,844; and 4,865,989).

The nucleic acid molecule can be incorporated or inserted into the yeast cell by known methods. For example, a suitable method of transforming cells is electroporation. Methods for preparing such recombinant yeast cells are described in more detail in Sambrook et al., "*Molecular Cloning: A Laboratory Manual*", second edition, Cold Spring Harbor Laboratory Press, Cold Spring Harbor (1989) and Sherman, F., et al., "*Methods in Yeast Genetics*", Cold Spring Harbor Laboratory Press, Cold Spring Harbor, N.Y., (1986), for example. Suitable yeast transformation protocols are known to those of skill in the art. An exemplary technique as described by Hinnen et al., *Proc. Natl. Acad. Sci. USA* 75:1929 (1978), selects for Trp$^+$ transformants in a selective medium consisting of 0.67% yeast nitrogen base, 0.5% casamino acids, 2% glucose, 10 μg/ml adenine and 20 μg/ml uracil.

In yet another embodiment, the invention includes methods for preparing the transformed yeast cells of the invention which includes maintaining the cells under conditions suitable for expression of the G-protein coupled receptor and G-protein subunits as well as binding of the ligand or test agent to the cell surface receptor.

The yeast cell is maintained under suitable conditions for expression of the G-protein coupled receptor and Gα subunit. Generally, the cells are maintained in a suitable buffer and/or growth medium or nutrient source for growth of the cells and expression of the gene product(s). The growth media are not critical to the invention, are generally known in the art, and include sources of carbon, nitrogen, sulfur and glucose. Examples include a modified SLAD and SLARG media (Lorenz, M. C., et al., *EMBO J* 16:7008 (1997). The pH which can be selected is generally one tolerated by or optimal for growth for the yeast cell.

The invention also provides expression vectors containing nucleic acid sequences. Suitable vectors for use in yeast are well known in the art and are generally commercially available, or readily prepared by the skilled artisan. For example, a suitable plasmid for use in yeast is YRp7 (Stinchcombs, et al., *Nature* 282:39 (1979); Kingsman, et al., *Gene* 7:141 (1979); Tschemper, et al., *Gene* 10:157 (1980)). Additional vectors useful to practice the invention include, for example, plasmids which replicate and function independent of the yeast cells, bacteriophages, and integratable DNA fragments which can integrate into the yeast genome.

In a preferred embodiment, the G-protein coupled receptor is a mammalian transmembrane cell surface receptor comprising intracellular, transmembrane (characterized by highly hydrophobic regions in the sequence) and extracellular domains. Examples of preferred receptors are somatostatin, MC4, βadrenergic, α-adrenergic, luteinizing hormone, follicle stimulatory hormone, parathyroid hormone, oxytocin, vasopressin, insulin, glucagon, thyroid stimulating hormone, prolactin, calcitonin, dopamine, chemokine, angiotensin, serotonin, acetylcholine and glutamate. The term G-protein coupled receptor as used herein includes, but is not limited to, any subtypes of the specific receptors named herein, and mutants, deletions, and homologs thereof, as well as the nucleic acid sequences encoding the same.

The term "Gα protein" refers to the α-subunit of a heterotrimeric, intracellular, membrane associated G-protein which when inactive binds GDP and when active binds GTP. Activation of the heterotrimeric G-protein leads to the exchange of bound GDP on the Gα subunit for bound GTP and dissociation of the activated Gα subunit from the dimeric βγ-subunit.

In a preferred embodiment the transformed yeast cell expresses the nucleic acid sequences encoding the G-protein coupled receptor and Gα protein subunit as a fusion protein. Preferably, the transformed yeast cells constitutively express an exogenous (heterologous) nucleic acid construct encoding a mammalian G-protein coupled receptor or fragment thereof and a G-protein α-subunit, most preferably Gpa2 or a functionally equivalent protein. The term "heterologous" is intended to include nucleic acid sequences from organisms other than yeast (e.g., mammalian). The transformed yeast cell may or may not express the endogenous gene encoding Gpa2 and any mutation or homolog of the same; for example, the endogenous gene encoding Gpa2 can have a loss of function mutation. Additionally, the transformed yeast cells may or may not express the endogenous genes encoding the G-protein β- and γ-subunits, Ste4 and Ste18, respectively, and mutations or homologs of the same such as a loss of function mutation. In particular embodiments, the transformed yeast cell can have a deletion of the endogenous G-protein coupled receptor which is the cognate receptor for the Gα subunit present in the expressed fusion protein.

In heterotrimeric G-protein mediated signaling the a and βγ-subunits can contribute to signaling. STE4 and STE18 encode the β- and γ-subunits, respectively, which mediate G-protein coupled receptor signaling in the Gpa1-dependent yeast mating response pathway. Neither Ste4 or Ste18 are required for pseudohyphal growth (Liu, H., et al., *Science* 262:1741–1744 (1993)). Gpa2 does regulate pseudohyphal growth (Kübler, E., et al., *J. Biol. Chem.* 272:20321–20323 (1997); Lorenz, M. C., et al., *EMBO J.* 16:7008–7018 (1997)). In addition, strains that have been deleted for other putative β- or γ-subunits have been constructed, and these strains do not display defects in pseudohyphal growth (Lorenz, M. C., et al., *EMBO J.* 16:7008–7018 (1997)). Together these findings suggest that Gpa2 signaling is a Ste4- and Ste18-independent process, and that other β- and γ-subunits remain to be identified (or that Gpa2 signalling does not require β- or γ-subunits). In order to determine the role(s) of Ste4 and Ste18 in the Gpa2-dependent response (e.g., cAMP response), the coding sequence for STE4 and STE18 can be deleted in haploid gpa2 strains.

The phrase "loss of function mutation" is intended to include any mutation which results in less than maximal function compared to the wildtype gene product including any reduction in or total absence of function. The term "mutation", as used herein, refers to any modification in the nucleic acid sequence of, e.g., the α-subunit of a G-protein. For example, the mutation can be a point mutation or the addition, deletion and/or substitution of one or more nucleotides. Modifications can be, for example, conserved or non-conserved, natural or unnatural. In one embodiment, the GTPase domain of the Gα protein (e.g., Gpa2) has a mutation resulting in a constitutively activated Gα subunit. Constitutive mutations cause genes which are normally regulated to be expressed without regulation, in some cases continuously. Amino acids of the native or wildtype sequence appropriate for substitution, deletion or conservation can be identified, for example, by sequence alignment between related Gα subunit proteins.

In a particular embodiment the nucleic acid constructs or expression vectors of the invention comprise a first nucleic acid sequence encoding a G-protein coupled receptor (e.g., somatostatin receptor) operably linked to a second nucleic acid sequence encoding a Gα subunit which is not a cognate protein of the mammalian G-protein coupled receptor (e.g., Gpa2). The term "cognate" as used herein refers to a G-protein which is normally functionally linked (coupled) to the G-protein coupled receptor in the signal transduction pathway such that the G-protein is activated and mediates a cellular response. Thus, non-cognate G-protein coupled receptors and G-protein pairs are those which either cannot associate with one another or which can associate but cannot mediate an intracellular response.

The two linked nucleic acid sequences which encode the fusion protein comprising the G-protein coupled receptor and the G-protein are downstream of a promoter, and preferably the nucleic acid sequence encoding the Gα subunit is downstream of the nucleic acid sequence encoding the G-protein coupled receptor. "Downstream" is a term of art used to refer to the direction of transcription. A nucleic acid sequence (e.g., a nucleic acid sequence encoding a Gα protein) being transcribed after another nucleic acid sequence (e.g., a nucleic acid sequence encoding a G-protein coupled receptor) is referred to as "downstream" of the later.

Nucleic acid constructs encoding mammalian G-protein coupled receptors and yeast Gα subunits are operably linked such that a fusion protein is expressed. "Operably linked" is intended to mean that the nucleotide sequence(s) is linked to a regulatory sequence in a manner which allows expression of the nucleic acid sequence(s).

Thus, mammalian G-protein coupled receptors and Gα subunits, preferably Gpa2, encoded by the nucleic acid sequences of the invention are expressed as a chimeric or fusion protein. Gpa2 can be linked to the G-protein coupled receptor in the cytoplasmic domain of the receptor by methods described herein. It is generally preferred that the amino-terminus of the Gα subunit is linked to the carboxy-terminus of the intracellular domain of the receptor to produce a fusion protein. Experimental conditions suitable for the construction of appropriate nucleic acid constructs and expression of the G-protein coupled receptor and Gpa2 fusion protein are well known in the art. Generally commercially available kits can be used and appropriately modified by one of ordinary skill. Exemplary methods to successfully produce fusion proteins are also described in detail in several art-recognized laboratory protocol textbooks, for example, Sambrook et al., *"Molecular Cloning: A Laboratory Manual"*, second edition, Cold Spring Harbor Press, Cold Spring Harbor (1989) and Ausubel et al., *"Current Protocols In Molecular Biology"*, John Wiley & Sons, (1998). In a preferred embodiment, the fusion protein is expressed and the G-protein coupled receptor portion integrated into the yeast plasma membrane in a manner compatible with a conformation suitable for ligand binding and transduction of the ligand-receptor binding signal.

The G-protein coupled receptor and G-protein can be directly bound together or indirectly bound together through a linking moiety. A linking moiety can be employed to link the G-protein coupled receptor and G-protein. The linker can preferably be a flexible linker and sufficient in length to separate the G-protein coupled receptor and G-protein in space, thereby not restricting the ability of the receptor and G-protein to maintain proper conformation, and not interfering with receptor-ligand binding or G-protein activation. The linker can be a peptide which can link the carboxy-terminus of G-protein coupled receptor to the amino-terminus of the G-protein. Preferred peptide linkers can be obtained from immunoglobulin hinge regions, such as a proline rich region. Appropriate linkers are characterized by low steric hindrance, thereby permitting maximal independent folding and cell membrane association of the G-protein coupled receptor and G-protein, such as with a polyglycine linker. The length of the linker is not particularly critical. Typically, the length of the linker can be between approximately two or approximately twenty amino acids. The selection of the particular linking group is not critical to the invention and within the technical expertise of one of ordinary skill in the art.

Many nucleic acid molecules coding for suitable mammalian G-protein coupled receptors, e.g., somatostatin and MC4, and G-protein α-subunits, e.g., GPA2, are known in the art and can be obtained from, for example, the EMBL/GenBank data bases. Such nucleic acid sequences can comprise both exons and introns in some instances. Alternatively, other sequences can be employed, such as homologs of related genes which are structurally or functionally equivalent to GPA2.

The phrase "functionally equivalent" as used herein refers to any nucleic acid sequence and its corresponding protein which mimics the biological activity of Gpa2 (e.g., phenotypic changes in yeast cells or alterations in transcriptional profiles of Gpa2-responsive genes attributed to activation of wildtype Gpa2) or which exhibit nucleotide or amino acid sequence identity to Gpa2. In one embodiment, the nucleic acid molecule shares at least about 40% sequence identity with the corresponding native sequence, preferably, at least about 60% sequence. In a more preferred embodiment, the percent sequence identity is at least about 80%, and still more preferably, at least about 95%. For example, phenotypic changes attributed to Gpa2 include pseudohyphal development in Saccharomyces cerevisiae through a cAMP-dependent mechanism following activation of adenylate cyclase (Nakafuku, M., et al., Proc. Natl. Acad. Sci. U.S.A. 85:1374–1378 (1988); Kübler, E., et al., J. Biol. Chem. 272:20321 (1997); Lorenz, M. C., et al., EMBO J. 16:7008–7018 (1997)). Increased cAMP production stimulates filamentous growth of diploid strains on low-nitrogen medium, augments the ability of haploid strains to invade a solid agar medium and increases glycogen accumulation in cells (Kübler, E., et al., J. Biol. Chem 272:20321 (1997)), Lorenz, M. D., et al., EMBO J. 16:7008 (1997). As such, activation of a GPA2 functionally equivalent gene would result in elevated cAMP in the transformed yeast cells leading to pseudohyphal growth when plated on low ammonium medium plates, invasion of solid agar and increased cellular stores of glycogen. Methods to score filamentous growth, monitor agar plate invasion and measure glycogen are routine procedures and known to the skilled artisan (See, for example, Gimeno, C. et al., Cell 68:1077 (1992); Lorenz, M. C., et al., EMBO J. 16:7008 (1997); Kübler, E., et al., J. Biol. Chem. 272:20321 (1977)). Also encompassed by the invention are naturally occurring GPA2 homologues, particularly those isolated from fungi.

At the molecular level, functionally equivalent GPA2 genes can be determined by comparisons of transcriptional profiles attributed to Gpa2 activation or based on sequence identity to GPA2. Sequence identity can be determined using database search strategies well known in the art including, for example, Basic Local Alignment Search Tool (BLAST) (Altschul, S. F., et al., J. Mol. Biol. 215:403–410 (1990)) and FASTA (Pearson, W. R., et al., Proc. Natl. Acad. Sci. U.S.A. 85:2444–2448 (1988)) algorithms. As described in detail in the Exemplification, transcriptional profiling can be used to determine the expression of specific subsets of yeast genes which are altered by activation of GPA2 linked to a G-protein coupled cell surface receptor upon ligand binding and receptor activation.

The term "alteration" in regard to activity or "altered activity" is defined herein as activity different from that of the wildtype. For example, in wildtype yeast, Gpa2 induces pseudohyphal growth, elevated cAMP levels and decreased glycogen deposition (Nakafuku, M., et al., Proc. Natl. Acad. Sci. U.S.A., 85:1374–1378 (1988); Kübler, E., et al., J. Biol. Chem. 272:20321–20323 (1997); Lorenz, M. C., et al., EMBO J. 16:7008–7018 (1997)). Functionally equivalent GPA2 genes can encode polypeptides which also induce, for example, pseudohyphal growth, adenylate cyclase activation and cAMP levels, and decrease glycogen deposition. Activation by a ligand can result in alterations in Gpa2 activity, or the activity of a polypeptide encoded by a functionally equivalent gene, which lead to decreased biological activity relative to wildtype Gpa2 to, for example, decrease pseudohyphal growth, adenylate cyclase activation and cAMP levels, and increase glycogen deposition. Alterations in Gpa2 activity can also result from the activity of agonists and antagonists.

Structurally or functionally equivalent genes can be homologous to GPA2. Such homologous nucleic acids, including DNA or RNA, can be detected and/or isolated by specific hybridization (e.g., under high stringency conditions). "Stringency conditions" for hybridization is a term of art which refers to the conditions of temperature and buffer concentration which permit hybridization of a particular nucleic acid to a second nucleic acid; the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 and pages 6.3.1–6 in Current Protocols in Molecular Biology (Ausubel, F. M. et al., "Current Protocols in Molecular Biology", John Wiley & Sons, (1998)) the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology,* 200:546–556 (1991). Also, in, Ausubel, et al., *"Current Protocols in Molecular Biology"*, John Wiley & Sons, (1998), which describes how to determine washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

Also encompassed by the present invention are the use of the transformed yeast cells for identifying agents which alter G-protein coupled receptor function. In a preferred embodiment, the receptors are mammalian receptors. The agents can be agonists or antagonists of the native (wildtype) ligand for the G-protein coupled receptor. Such agents can be polypeptides (including post-translationally modified proteins) or small molecules (including sugars, steroids, lipids, anions or cations).

The term "antagonist", as used herein, refers to an agent which blocks, diminishes, inhibits, hinders, limits, decreases, reduces, restricts or interferes with native ligand binding to its G-protein coupled receptor, or alternatively and additionally, prevents or impedes the cellular effects associated with ligand-G-protein coupled receptor binding thereby preventing activation of the Gα subunit. By way of example, an antagonist of Gpa2 activation will decrease adenylate cyclase activity and cAMP levels in the cell leading to phenotypic (e.g., decreased pseudohyphal growth) and molecular (e.g., decreased transcription of Gpa2-responsive genes) changes.

The term "agonist", as used herein, refers to an agent which augments, enhances, increases, intensifies or strengthens native ligand binding to the G-protein coupled receptor, or alternatively and additionally, mimics or simulates the effect of the native ligand-G-protein coupled receptor binding on the target cell thereby activating the Gα subunit. In the case of Gpa2, an agent possessing agonist activity will increase adenylate cyclase activity and cAMP levels leading to increased pseudohypal growth and activation of Gpa2-responsive genes.

The transformed yeast cells expressing the mammalian cell surface G-protein coupled receptor and the yeast Gα subunit, preferably Gpa2, fusion protein are obtained by transforming the yeast cell with nucleic acid constructs of this invention under appropriate regulatory control to result in the expression of cell-surface receptors linked to Gα subunits. The test agent (e.g., an agonist or antagonist) is added to the transformed yeast cells under conditions suitable for maintaining expression of the G-protein coupled receptor in a conformation appropriate for association of the test agent or ligand and receptor. For example, conditions for evaluating agents, such as media and temperature requirements, can, initially, be similar to those necessary for binding of the native ligand to the G-protein coupled receptor. One of ordinary skill in the art would know how to vary experimental conditions depending upon the biochemical nature of the test agent. The test agent can be added to the transformed yeast cell in the presence or absence of native ligand for the G-protein coupled receptor. The concentration at which the test agent can be evaluated can be similar, more, or less than concentrations employed by the native ligand to bind receptor.

Thus, the invention relates to a method for identifying agents which alter G-protein coupled receptor activation comprising providing the test agent to the transformed yeast cell, under conditions suitable for binding, wherein the transformed yeast cell comprises a mammalian G-protein coupled receptor operably linked to a Gα subunit (e.g., Gpa2) in a fusion protein. Dissociation of the Gα subunit, preferably Gpa2, from the dimeric βγ-subunit can be detected by phenotypic alterations in the transformed yeast cell, for example, pseudohyphal growth, glycogen deposition and penetration in agar; and additionally or alternatively, changes in the transcriptional profiles of Gpa2-dependent genes. Dissociation of the Gα subunit can also be ascertained chromatographically to determine the proportion of α-, β- and γ-subunits or enzymatically by assaying for GTPase activity using established protocols described, for example, by King et al., U.S. Pat. No. 5,482,835 (1996) and Pausch et al., U.S. Pat. No. 5,691,188 (1997).

G-protein activation of cAMP dependent signal transduction can also be indicated by the use of reporter genes. In another embodiment of the invention, a nucleic acid construct comprising a Gpa2-responsive promoter operably linked to a nucleic acid construct encoding a reporter gene can be used to detect Gα protein activation. Gpa2-responsive promoters can be identified by transcription profiling as described in the Exemplification. Preferably the Gpa2-responsive promoter (e.g., a cAMP responsive promoter) is a promoter of a gene selected from the group consisting of YMR323w, YBL100c, YDR187c, YEL045c, YBLO96c, YNL028w, YFR056c, PHO4, YCL046w, YCLX09w, YPL281c, YJL045w, YGL046w, GLK1, YML058c-a, YJR114w, IDH2, YML035c-a, HSP12, HSP26, YNL134c and YML128c. Following G-protein coupled receptor activation of the Gα subunit, for example by ligand binding, the activity of Gpa2-responsive promoters or cAMP production or a combination of both can be detected. For example, reporter gene expression can be induced or repressed under appropriate conditions, or transformed yeast cells which have elevated intracellular levels of cAMP as a result of G-protein activation, can be identified. Experimental induction, repression, and detection of reporter genes are well known in the art.

A further embodiment includes the use of a third heterologous nucleic acid sequence comprising a promoter comprising at least one STRE sequence operably linked to a reporter gene. Gpa2 represses the transcription of genes which contain STREs (FIGS. 4, 5, and 6). The core sequence for an STRE is 5'-CCCCT-3' (Ruis, H., et al., *BioEssays* 17:959–965 (1995); Siderius, M., et al., *"Yeast Stress Responses"* pages 213–230, Hohmann, S., et al., (eds.), Landes, Austin, Tex. (1997)). In this case, following activation of the Gα subunit, the repression of transcription from genes containing STRE(s) can be detected using reporter gene strategies as described herein. It is envisioned that the STRE sequences can be derived from nature or synthetically produced using recombinant DNA technologies based on known STRE sequences.

The addition of ligand to transformed yeast cells expressing G-protein coupled receptor-Gpa2 fusion protein can elicit a transcriptional response that is similar to the response stimulated by activation of Gpa2 in wild type cells. To determine whether this system is functioning at maximal potential, plasmids designed to express fusion proteins that link Ste2 to both constitutively active and constitutively inactive forms of Gpa2 can be constructed and expression can be regulated by the PGK promoter. These fusion proteins can provide maximal and minimal induction of Gpa2 signaling, respectively.

Transcriptional profiling of transformed yeast cells expressing a Ste2-Gpa2 fusion protein has identified several genes whose expression is repressed in a ligand-dependent manner. Upstream regulatory sequences from these genes can be fused to reporter proteins (e.g., enzymes, auxotrophic markers), and these reporter constructs may be used to screen for activation of Gpa2 signaling. Approximately 1500 base pairs of promoter sequence from several genes regulated by Gpa2 have been amplified. The amplified product includes the translation initiation sequences and the first five base pairs of coding sequence for each predicted protein. These fragments have been cloned in-frame to coding sequence for the bacterial enzyme β-galactosidase. Promoter-lacZ fusions can be constructed in a low-copy and multi-copy vectors using YMR323w, YBL100c, YDR187c, YEL045c, YBLO96c, YNL028w, YFR056c, PHO4, YCL046w, YCLX09w, YPL281c, YJL045w, YGL046w, GLK1, YML058c-a, YJR114w, IDH2, YML035c-a, HSP12, HSP26, YNL134c and YML128c. These putative reporter constructs can be transformed into yeast strains in order to assay for Gpa2-dependent regulation of β-galactosidase activity.

Also within the scope of the invention is the use of heterologous nucleic acid constructs comprising Gpa2-responsive promoters operably linked to reporter genes. As discussed in detail in the Exemplification, transcriptional profiling has identified several genes that are repressed by Gpa2 activation. The promoter regions of these genes have been sequenced and can be used to monitor activation of G-protein coupled receptor/Gpa2 signal transduction activation pathways. In a preferred embodiment the Gpa2-responsive promoter is YMR323w or YBL100c or YDR187c or YEL045c or YBLO96c or YNL028w or YFR056c or PHO4 or YCL046w or YCLX09w or YPL281c or YJL045w or YGL046w or GLK1 or YML058c-a or YJR114w or IDH2 or YML035c-a or HSP12 or HSP26 or YNL134c or YML128c or any combination thereof.

Signals transduced through heterologous G-protein coupled receptors and Gpa2 can also be detected by the use of heterologous effectors (e.g., adenylate cyclase). "Effector" as used herein refers a molecule(s) (e.g., polypeptide such as adenylate cyclase, lipid, anion or cation) that is responsible for the generation of a second messenger (e.g., cAMP, cGMP, calcium, diacylglycerol). For example, ligand-dependent activation of a G-protein coupled receptor linked to Gpa2 can be determined by activation of a nucleic acid construct encoding adenylate cyclase, guanylate cyclase, or phospholipase C-β, or any combination thereof, operably linked to a reporter gene.

Another aspect of the invention relates to the identification of genes which are responsive to G-protein coupled receptor activation of a Gα subunit, preferably Gpa2, wherein the resultant effector is adenylate cyclase, guanylate cyclase, or phospholipase C-β, or any combination thereof; and the resultant second messenger is cAMP, cGMP, diacylglycerol, inositol triphosphate, or calcium or any combination. A ligand of the receptor can be contacted with the transformed yeast cells expressing the mammalian G-protein coupled receptor/Gpa2 fusion protein of the invention. Differences in the expression of ligand-responsive genes can be detected by determining and comparing the difference in gene expression in the presence and absence of ligand. Conditions appropriate for ligand-receptor binding can be determined based on the nature of the receptor and ligand. Detection methods employed for defining differences in expression that are Gpa2- and cAMP-dependent include comparisons of transcriptional profiles of strains grown in the presence and absence of ligand, as well as phenotypic changes.

The invention shows that expression of heterologous G-protein coupled receptor-Gpa2 fusion proteins can activate Gpa2-dependent (e.g., cAMP-dependent) responses in yeast in a ligand-dependent manner. Transcriptional profiling can demonstrate that expression of similar subsets of yeast genes is either induced or repressed both by a constitutively active form of Gpa2 as well as by the addition of ligand to a transformed yeast cell expressing a G-protein coupled receptor-Gpa2 fusion protein. In addition, at least a subset of these genes whose expression is repressed by activation of GPA2 is known to be repressed by the yeast cAMP response. Expression of heat shock protein 12 (HSP12) is reduced in the presence of high levels of cAMP (Varela, J. C., et al., *Mol. Cell. Biol.* 15:6232–6245 (1995)). HSP 12 and HSP26 contain promoter stress response elements (STREs) (Varela, J. C., et al., *Mol. Cell. Biol.* 15:6232–6245 (1995); Gounalaki, N., et al., *EMBO. J.* 13:4036–4041 (1994)). High levels of cAMP are expected to decrease the expression levels of genes containing STREs (Gorner, W., et al., *Genes & Dev.* 12:586–597 (1998); Varela, J. C., et al., *Mol. Cell. Biol.* 15:6232–6245 (1995); Marchler, G., et al., *EMBO J* 12:1997–2003 (1993)). An analysis of upstream regulatory sequences of the entire set of genes identified by transcriptional profiling as genes whose expression is repressed by Gpa2 activation has revealed promoters of several of these genes contain putative STREs (FIG. 6). Promoters from genes containing the STREs, as well as the remaining genes whose expression is repressed by GPA2 activation, can be used to drive the expression of reporter genes that can serve as a means to assay for induction of the yeast cAMP response by ligand dependent activation of a G-protein coupled receptor coupled to Gpa2. Furthermore, the general strategy of comparing transcriptional profiles from transformed yeast cells expressing constitutively active alleles of G-protein α-subunits to profiles of ligand activated G-protein coupled receptor-Gα subunit fusion proteins can be of general use for establishing Gpa2-independent systems for studying heterologous G-protein coupled receptors in yeast. Thus, a constitutively active G-protein α-subunit (yeast or heterologous) expressed in a transformed yeast cell can elicit a cellular response that can be monitored using transcriptional profiling. Therefore, it is possible to design strategies to use transformed yeast cells to study coupling of heterologous G-protein coupled receptors to heterologous G-protein α-subunits (e.g., through fusion proteins).

The following Examples are offered for the purpose of illustrating the present invention and are not to be construed to limit the scope of this invention. The teachings of all references cited herein are hereby incorporated herein by reference.

Exemplification

Strains and Media

Standard yeast media and microbiological techniques were used (Sambrook, J. E. F., et al., "*Molecular Cloning:*

A Laboratory Manual", second edition, Cold Spring Harbor Laboratory Press, Cold Spring Harbor (1989); Sherman, F., et al., "Methods in Yeast Genetics", Cold Spring Harbor Laboratory Press, Cold Spring Harbor, N.Y. (1986)). SLAD media was prepared as previously described (Gimeno, C. J., et al., Cell 68:1077–1090 (1992)).

Yeast strains used in this study are listed in FIG. 2. All strains are derived from either the Σ1278b or YPH501 genetic backgrounds. The hisG::URA3::kan$_r$::hisG disruption cassette from plasmid pSE1076 was used to create GPA2 and RAS2 null alleles (pSE1076 from S. Elledge, Baylor College of Medicine, Houston, Tex.). The disruption cassette is contained within a 5 kB BglII-BamHI restriction fragment isolated from pSE1076. PCR was performed on yeast genomic DNA to amplify approximately 500 base pairs of sequence upstream and downstream of the GPA2 and RAS2 coding sequence.

Oligonucleotides used to construct the GPA2 deletion construct were:

```
                                             (SEQ ID NO: 1)
5'-ACGCGTCGACGATAGGAACAATACGACAAGGG-3';

(SEQ ID NO: 2)
5'-CGCGGATCCCAGAGACCCATGATATTTGCTTG-3';

(SEQ ID NO: 3);
5'-CGCGGATCCGTGTTACAATGAATGCACAGCTA-3';

and
                                             (SEQ ID NO: 4)
5'CCTAGGCGAGCTCTCCGCATTCAAAAGCTCCTG-3'.
```

Oligonucleotides used to construct the RAS2 deletion construct were:

```
                                             (SEQ ID NO: 5)
5'-ACGCGTCGACACGGGCGTGGCCGTATCAATG-3';

(SEQ ID NO: 6)
5'-CGCGGATCCTCTGTATATCTCCTTTCAAT-3';

(SEQ ID NO: 7)
5'-CGCGGATCCGGCTGTTGTATTATAAGTTAA-3';

and
                                             (SEQ ID NO: 8)
5'-CCTAGGCGAGCTCGATTATCGTCCTCACCGGCAT-3'.
```

Restriction sites were introduced into the oligonucleotide primers in order to yield amplification products <SalI-upstream sequence-BamHI> and <BamHI-downstream sequence-SacI>. A four part ligation into SalI/SacI digested Bluescript SK+(Stratagene, La Jolla, Calif.) was performed to create GPA2 and RAS2 deletion constructs. Deletion constructs were digested with SalI and SacI, deletion fragments were purified, and DNA was transformed into yeast. Proper integrants were confirmed by PCR analysis using primers internal to the hisG::URA3::kanr::hisG disruption cassette and primers with homology to genomic sequence further upstream or downstream to that amplified for the deletion construct.

Strain MMB1190 was sequentially grown and diluted into fresh rich medium in order to achieve sufficient mitotic growth such that mitotic recombination events could be detected between the hisG repeats, resulting in the loss of the URA3 sequence from the genomic GPA2 locus (producing MMB1191).

Plasmid Construction

Microbiological techniques were performed using well-established protocols (Sambrook, J. E. F., et al., "Molecular Cloning: A Laboratory Manual", 2nd edition, Cold Spring Harbor Laboratory Press, Cold Spring Harbor (1989)). Plasmids (except deletion constructs) were sequenced to eliminate the possibility of mutations being introduced during PCR or cloning.

The low-copy plasmid pRS415 (Sikorski, R., et al., Genetics 122:19–27 (1989)) was used to create a series of constructs that contained a coding sequence for either GPA2, an activated allele of GPA2 (GPA2Q300>L), or GPA2/GPA1, which encodes a chimeric protein. A 419 base pairs of GPA2 upstream regulatory sequence was used to drive expression in all of these constructs.

pRS415-GPA2 was created in a multi-step cloning procedure into pRS415. Oligonucleotides 5'-AAAACTGCAGCGGGTAACCCGTGGTACCC-GGGGC-3' (SEQ ID NO: 9)and 5'-CTAGTCTAGAATTGTCGAAGCAGTGGATCCATTTT-3' (SEQ ID NO: 10) were used to amplify a fragment containing 419 base pairs of GPA2 promoter and the first 938 base pairs of GPA2 coding sequence. The 938 base pair fragment of the GPA2 coding sequence contains an A to C substitution at base 924 of coding sequence which creates a BamHI site that does affect the predicted Gpa2 protein sequence. The fragment containing the GPA2 promoter and 930 base pairs of coding sequence was digested with SmaI and XbaI, and cloned into pRS415.

The primers 5'-CGCGGATCCACTGCTTCGAC-AATGTCAC-3' (SEQ ID NO: 11) and 5'-CTAGTCTAGATGTTACCCGGGATAATAACTATA-3' (SEQ ID NO: 12) were used to amplify a fragment that contains the final 431 base pairs of GPA2 coding sequence and 279 base pairs of downstream sequence. This PCR product was BamHI/XbaI digested and cloned into the truncated GPA2 construct described above. The resulting plasmid contains full-length GPA2 with a silent BamHI site introduced, and transcription and translation signals are provided by GPA2 regulatory sequences.

Low-copy pRS415-GPA2/GPA1 was created by sequential cloning experiments. pRS415-GPA1 was constructed by amplifying the GPA1 coding sequence together with 201 base pairs of upstream sequence and 304 base pairs of downstream sequence. This fragment with the GPA1 coding and regulatory sequence was cloned into the EcoRI site of pRS415 to generate pRS415-GPA1.

Oligonucleotide pairs 5'-TCAACTTGACTGTGATGATCCGATC-3' (SEQ ID NO: 13)/5'-TCCTTCGAAACAATGATCCACTTCT-3' (SEQ ID NO: 14) and 5'-AGAAGTGGATCCATTGTTTCGAAGGA-3' (SEQ ID NO: 15)/5'-TCTGCATCGCCGACACGTCC-3' (SEQ ID NO: 16) then were used to amplify two fragments (705 and 278 base pairs, respectively) of GPA1 coding sequence that overlap by 36 base pairs. The oligonucleotides have introduced a BamHI site into the GPA1 coding sequence within this overlapping region. The overlapping fragments were then incubated together and thermocycling was performed using Pfu polymerase to generate a single 947 base pair fragment. Outside primers 5'-TCAACTTGACTGTGATGATCCGATC-3' (SEQ ID NO: 17) and 5'-TCTGCATCGCCGACACGTCC-3' (SEQ ID NO: 18) were then used to amplify the 947 base pair product. The resulting product was SphI digested and cloned into the pRS415-GPA1 plasmid described above from which a 850 base pair SphI fragment of GPA1 coding sequence had been deleted.

This cloning strategy created a full-length GPA1 clone that contains a BamHI site. The BamHI site resides in the same frame and predicted functional peptide domain in both this construct and the GPA2 BamHI construct described above. These BamHI mutations can be used to create chimeric Gpa2/Gpa1 proteins.

The pRS415-GPA1 BamHI plasmid was BamHI/SmaI digested, and the fragment containing the coding sequence for the carboxy-terminus of Gpa1 was gel purified. The pRS415- truncated GPA2 BamHI plasmid described above was digested with XbaI, made flush with the Klenow fragment, and then digested with BamHI. The BamHI/SmaI GPA1 fragment was then ligated to the truncated GPA2 to create the chimeric GPA2/GPA1 construct.

The pRS415-GPA2Q300>L was created by performing site-directed mutagenesis on pRS415-GPA2. Overlapping oligonucleotides 5'-ACGTGGGTGGACTGCGTTCCGAAAG-3' (SEQ ID NO: 19) and 5'-CTTTCGGAACGCAGTCCACCCACGT-3' (SEQ ID NO: 20) were used to introduce a substitution at codon 300. These oligonucleotides were annealed to pRS415-GPA2 and twelve rounds of thermocyling were performed using Pfu polymerase. Plasmids were denatured at 94° C. for 30 seconds, oligonucleotides were annealed at 50° C. for 1 minute, and extensions proceeded 16 minutes at 68° C. The DNA was DpnI digested for 2 hours, purified, and transformed into E. coli. Plasmids were recovered and sequenced to confirm that the specific mutation had been introduced.

Plasmid PGK-STE2 was constructed in the pYPGE2 plasmid that allows transcription to be controlled by the strong PGK promoter (Brunelli, J. P., et al., Yeast 9:1299–1308 (1993)). Oligonucleotides 5'-AGCGGATCCAAAAAAATGTCTGATGCGGCTCCTTC-3' (SEQ ID NO: 21)(contains translation initiation sequence) and 5'-AGCAGTGGCGCCTGAATCTAGTAGTAA-CCTTATACC-3' (SEQ ID NO: 22) were used to amplify STE2 coding sequence from genomic DNA. The amplified product was BamHI/NarI digested and cloned into pYPGE2 vector that had been BamHI/ClaI digested. Plasmid PGK-STE2 was used to generate PGK-STE2-GPA2 and PGK-STE2-GPA2/GPA1. PGK-STE2 was BamHI/PstI digested and the fragment containing STE2 coding sequence was gel purified.

Oligonucleotide pairs 5'-ACCGCTGCAGATGGTCTCTGCGCATCTTCAGAA-3' (SEQ ID NO: 23)/5'-CCGCT-CGAGGTCGACGCTGTGCATTCATTGTAACACTCC-3' (SEQ ID NO: 24) and 5'-ACCGCTGCAGATGGTCTCTGCGCATCTTCAGAA-3' (SEQ ID NO: 25)/5'-CCGCTC-GAGGTCGACCAGTTCCTTCATATAATACCA-3' (SEQ ID NO: 26) were used to amplify GPA2 and GPA2/GPA1 coding sequence, respectively. The resulting PCR products were PstI/SalI digested. Finally, pYPGE2 was BamHI/SalI digested and used in a three part ligation with the STE2 and GPA2 (or GPA2/GPA1) fragments described above.

The GPA2 PstI/SalI fragment described above also was used to create a fusion with the rat somatostatin receptor (SSTR2). Primers 5'-CGTGTCGACA-GATCTAAAAAATGGAGATGAGCTCTGAG-3' (SEQ ID NO: 27) and 5'-TCGCTC-GAGGTCGACTCAGATACTGGTTTGGAGGT-3' (SEQ ID NO: 28) were used to amplify rat SSTR2 from rat genomic DNA. The fragment of the rat SSTR2 coding sequence was BglII/SalI digested and cloned into pYPGE2 BamHI/SalI.

Primers 5'-CGTGTCGACAGATCTAAAAATGGAGAT-GAGCTCTGAG-3' (SEQ ID NO: 29) and 5'-CTCCGCTGCAGCGATACTGGTTTGGAGGTCTCC-3' (SEQ ID NO: 30) were then used to amplify a rat SSTR2 coding sequence from pYPGE2-rSSTR2 with BglII and PstI restriction sites at the end. pYPGE2 was BamHI/SalI digested and used in a three part ligation with the rSSTR2 BglII/PstI and GPA2 PstI/SalI.

Glycogen Staining and Psdeudohyphal Growth Assays

Glycogen staining was performed essentially as described (Toda, T., et al., Cell 40:27–36 (1985)). Strains were streaked on plates and generally grown for two days. Iodine crystals were placed in a glass dish situated above a beaker of heated water. Plates containing strains were exposed to iodine vapors until strains were stained.

Pseudohyphal growth experiments were performed as described (Gimeno, C. J., et al., Cell 68:1077–1090 (1992)). Cells were either streaked at very low density or spotted (10 µl containing approximately 100 cells) on SLAD plates, and growth and cell morphology were monitored periodically for one week. Various concentrations (1 µg, 10 µg or 100 µg) of a factor were spread over SLAD plates for experiments that involved signalling by the Ste2 receptor.

Preparation of Cultures and RNA for Transcriptional Profiling

In experiments involving PGK-STE2 and pRS415-GPA2/GPA1 yeast strains (MMB1205, MMB1209, MMB1207, MMB1210) were grown overnight, diluted to $OD_{600}$=0.2, treated with 3 µg/ml α factor, and grown at 30° C. for 3 and 6 hours. Cells were harvested and RNA was prepared. For subsequent experiments using either PGK-STE2-GPA2 (MMB1211) (Experiments 2, 3 and 4; FIG. 5), PGK-STE2-GPA2/GPA1 (MMB1212)(Experiment 4; FIG. 5), or PGK-rSSTR2-GPA2 (MMB1280) (Experiment 2; FIG. 5 (data not shown))the strains were grown overnight, diluted to $OD_{600}$= 0.15, grown for 3 hours at 30° C., treated with ligand (9 µg/ml of α factor or 5.4 µM somatostatin S14). After growth for an additional 3 hours at 30° C., the cells were harvested and RNA prepared for transcriptional profiling.

In one series of experiments strains MMB1210 and MMB1207 (Experiment 4; FIG. 5) were used to obtain profiles of strains with an activated Gpa2 signalling pathway. These strains were also treated with α factor.

In another series of experiments yeast strains MMB1274 and MMB1276 were used to provide a readout of GPA2 dependent transcriptional activation (Experiments 2 and 3; FIG. 5) (Varela, J. C., et al., Mol. Cell. Biol. 15:6232–6245 (1995)). These strains were not treated with either α factor or somatostatin S14. Yeast strains MMB1194, MMB1203, and MMB1204 were used in transcriptional profiling experiments performed to compare the effects of GPA2 activation in synthetic complete medium versus SLAD medium. (Experiment 1; FIG. 5) Yeast strains were grown overnight, diluted to $OD_{600}$=0.2, allowed to grow at 30° C. for 3 hours, washed in deoinized water and diluted to an $OD_{600}$=0.2 or $OD_{600}$=0.6 in synthetic complete medium and SLAD medium, respectively. The difference in the concentration of yeast cell is due to the differential growth of yeast in complete synthetic and SLAD medium. After 3 hours of growth at 30° C., cells were harvested and RNA prepared for analysis by transcriptional profiling.

Total yeast RNA was prepared by isolation using TRIzol reagent (GIBCO BRL, Grand Island, N.Y.). Yeast culture medium (10–20 ml) was harvested by centrifugation, the supernatant removed, cells resuspended in TRIzol reagent in the presence of zirconium/silica beads, and the sample frozen in dry ice. Samples were thawed and homogenized in a Mini-Beadbeater (Biospec Products, Bartlesville, Okla.).

Samples were centrifuged at high-speed in a microcentrifuge and the aqueous phase removed. The aqueous phase then was extracted repeatedly with phenol/chloroform/isoamyl alcohol (25:24:1 vol) until there was no visible protein interface. A final chloroform/isoamyl alcohol extraction was performed and then isopropanol was used to precipitate RNA from the aqueous phase. The RNA precipitate was washed in 70% ethanol, dried briefly, and resuspended in DEPC-treated water. The RNA concentrations were calculated and RNA quality was assessed by electrophoresis of RNA in 1% agarose gels containing ethidium bromide.

Transcriptional Profiling

First strand cDNA synthesis was performed using the GIBCO BRL SuperScript PreAmplification System™ (Grand Island, N.Y.). cDNA was synthesized from approximately 10–15 μg total yeast RNA in the presence of $^{33}$P-dCTP. Labeling reactions were allowed to proceed 1 hour at 42° C. and then cDNA probes were purified using Chroma Spin-30 columns (CLONTECH Laboratories, Palo Alto, Calif.) in a clinical centrifuge. Labeling reactions then were stopped by the addition of EDTA (to approximately 0.5 mM final concentration and cDNA denatured by treatment with NaOH (approximately 25 mM final concentration) and incubation at 70° C. for 10 minutes.

Labeled cDNA probes were used to hybridize to gridded arrays of approximately 6000 yeast predicted open reading frames (ORFs). PCR products for yeast ORFs were purchased from Research Genetics and a common primer set was used to amplify these ORFs. PCR products were gridded in microarrays on Biodyne B nylon membranes (GIBCO BRL, Grand Island, N.Y.). Alkaline treatment was performed to denature PCR products on membranes, and after neutralization the membranes were baked at 80° C. for 30 minutes. Nylon microarrays were pre-hybridized and hybridized in Church blot solution (7% SDS, 0.5 M NaPO4, 1 mM EDTA, 0.5% casein Hammerstein (ICN Biomedicals Inc., Aurora, Ohio). Hybridizations were performed overnight at 68° C. Membranes were then washed in Church blot wash solutions, dried and baked at 80° C. until completely dry, and then exposed overnight to Fuji BAS-III S phosphoimager screens.

Hybridization data were obtained using a Fujifilm BAS-2500 phosphoimager and Fujifilm ImageReader software. Analytical Imaging Station (AIS) software (Imaging Research Inc., Brock University, St. Catherines, Ontario, Canada) was used to designate quantitative values to each spot on the microarray. All experiments were normalized such that the median yeast gene was expressed at a level of 100 units. These values could be used to calculate ratios that would represent relative expression changes for each predicted ORF throughout RNAs from various strains and ligand treatments.

The invention shows that expression of heterologous G-protein coupled receptors and Gpa2 fusion proteins can be a general strategy for constructing assays to study G-protein coupled receptors. For example, plasmids that encode fusion proteins linking the rat somatostatin receptor or the human MC4 receptor to Gpa2 have been constructed and transformed into yeast strains. Ligands for the somatostatin receptor and MC4 receptor are well-known and readily available. The transformed yeast cells of the invention comprising heterologous G-protein coupled receptor-Gpa2 fusion protein can be used to monitor ligand binding to various heterologous G-protein coupled receptors employing transcriptional (or reporter gene) readouts by the addition of ligand. The transcriptional readouts should be similar to that monitored by addition of α factor to a strain expressing the Ste2-Gpa2 fusion protein.

GPA2 Functions in the Yeast cAMP Response: Pseudohyphal/Invasive Growth, Glycogen Accumulation and Colony Morphology in gpa2Δ Strains Haploid gpa2Δ::URA3 (MMB1190); gpa2Δ::hisG (MMB1191) strains; and a homozygous diploid gpa2Δ::URA3/gpa2Δ::URA3 strain (MMB1193) were constructed in the Σ1278b genetic background (FIG. 2). A phenotypic analysis of these strains was performed. In particular, these strains were examined for defects in cellular functions known to be regulated by cAMP production. cAMP production has been shown to stimulate the filamentous growth of diploid strains on low-nitrogen medium and the ability of haploid strains to invade a solid agar medium (Gimeno, C. J., et al. , Cell 68:1077–1090 (1992); Kübler, E., et al., J. Piol. Chem. 272:20321–20323 (1997); Lorenz, M. C., et al., EMBO J. 16:7008–7018 (1997); Mosch, H. U., et al., Proc. Natl. Acad. Sci. 93:5352–5356 (1996); Ward, M. P., et al., Mol. Cell. Biol. 15:6854–6863 (1995)). Diploid gpa2 strains have impaired ability to form pseudohyphae after growth on solid medium containing low levels of nitrogen (Kübler, E., et al., J. Biol. Chem. 272:20321–20323 (1997); Lorenz, M. C., et al., EMBO J. 16:7008–7018 (1997)). After incubation on low ammonia SLAD plates for several days, gpa2 cells (MMB1194) were defective in pseudohyphal growth. Consistent with known observations, gpa2 strains are weak in their ability to form filaments.

Haploid gpa2 strains were also found to have several phenotypes. The gpa2Δ::URA3 and gpa2Δ::hisG strains display a previously unobserved colony morphology phenotype. Haploid Σ1278b strains develop an elaborate lacy colony morphology after several days of growth on YPAD plates. The gpa2 strains fail to develop a lacy morphology, and, instead, display a more rounded colony morphology.

In addition, haploid gpa2 strains display agar invasion defects. Haploid GPA2 (MMB1187), gpa2Δ::URA3 (MMB1190) and gpa2Δ::hisG (MMB1191) strains were plated for single colonies, grown for 5–7 days on YPAD plates, and then the plates were washed with deionized water. Wild-type, but not gpa2, strains were able to penetrate the solid agar substrate.

Accumulation of glycogen was another phenotype that was monitored. Glycogen accumulation has been shown to be inversely proportional to the accumulation of intracellular cAMP. Glycogen levels are readily assayed by exposure to iodine vapors (Toda, T., et al., Cell 40:27–36 (1985)). Haploid gpa2Δ::UPA3 (MMB1190) and gpa2Δ::hisG (MMB1191) strains both display subtle defects in glycogen accumulation, as previously noted (Kübler, E., et al., J. Biol. Chem. 272:20321–20323 (1997)). Thus, both diploid and haploid gpa2 strains display phenotypes that have been associated with strains that are impaired in the production of cAMP.

Genetic Interactions with cAMP Pathway Component RAS2

In yeast, Ras2 regulates the activity of adenylate cyclase and, thus, overall cAMP levels. Overexpression of GPA2 has been shown to suppress the growth defect of ras2$^{ts}$ strains (Nakafuku, M., et al., Proc. Natl. Acad. Sci 85:1374–1378 (1988)). Haploid ras2Δ::URA3 strains (MMB1200) were constructed in a YPH501 genetic background (MMB1197), mated to gpa2Δ::URA3 strains (MMB1199) (YPH501 background), and diploids sporulated and dissected. In four spore tetrads containing 2 URA$^+$ colonies, both the URA$^+$ colonies displayed an extreme growth defect at 30° C. The URA$^-$ colonies are expected to be ras2Δ::URA3 gpa2Δ::URA3 double mutants. Small colonies formed only after 5 days growth, and these strains are prone to develop suppressor mutations. These observations are in agreement with previous experiments performed in the Σ1278b genetic background (Kübler, E., et al., *J. Biol. Chem.* 272:20321–20323 (1997)). Therefore, GPA2 displays genetic interactions with a key component in the yeast cAMP response.

Constitutively Active Gpa2 Stimulates cAMP Production and Pseudohyphal Growth

In order to further characterize the function of Gpa2 an allele of GPA2 was constructed to maintain Gpa2 in the active, GTP-bound form. Similar mutations in the human stimulatory G-protein eliminate 95% of the GTPase activity (Graziano, M. P., et al., *J. Biol. Chem.* 264:15475–15482 (1989); Masters, S. B., et al., *J. Biol. Chem.* 264:15467–15474 (1989)).

A GPA2 Q300>L substitution was created in a low-copy vector. The substitution resides near the predicted nucleotide binding pocket of Gpa2. GPA2 Q300>L was expressed in both haploid (MMB1202) and diploid gpa2Δ (MMB1203) strains, and these strains were analyzed for effects in glycogen accumulation and pseudohyphal growth.

Strains expressing GPA2 Q>300L display a pronounced decrease in glycogen accumulation (e.g., high cAMP) when assayed by iodine staining. In addition, diploid gpa2 strains that express GPA2 Q>300L undergo pseudohyphal growth, and the extent of filament formation is more dramatic than that observed for the same strain expressing wild-type GPA2 (MMB1204) from the same vector. A similar result has been described for a GPA2 G132>V constitutively active form (Lorenz, M. C., et al., *EMBO J.* 16:7008–7018 (1997)). Thus, activation of GPA2 can be monitored, both in rich (e.g., glycogen accumulation) and low nitrogen (e.g., pseudohyphal growth) media. This suggested that if a system could be established for coupling of heterologous G-protein coupled receptors to Gpa2, then ligand dependent activation of Gpa2 could result in a readout (e.g., either phenotypic or transcriptional) that can be similar to that observed upon expression of the constitutively active form of Gpa2.

Coupling of Ste2 to Gpa2 in Diploid Cells as Test System

STE2 encodes a yeast G-protein coupled receptor that functions as the receptor for the mating pheromone a factor (Bardwell, L., et al., *Dev. Biol.* 166:363–379 (1994); Kurjan, J., *Annu. Rev. Biochem.* 61:1097–1129 (1993)). Ste2 signaling is mediated by the Gpa1 α-subunit, and STE2 is not normally expressed in diploid cells (Hwang-Shum, J. J., et al., *Mol. Gen. Genet.* 227:197–204 (1991)). The constitutive PGK promoter was used to express Ste2 in a diploid cell. Full-length STE2 was cloned into the YPGE2 vector to produce PGK-STE2 (pMB171) (Brunelli, J. P., et al., *Yeast* 9:1299–1308 (1993). PGK-STE2 can restore pheromone-responsiveness to a haploid ste2Δ strain. In addition, Northern blot analysis has determined that PGK-STE2 is expressed at high levels when transformed into diploid strains (MMB1210). Thus, expressing Ste2 in a diploid cell was selected for a feasibility study to determine whether Gpa2 and the cAMP response can be used as a system for studying coupling to heterologous G-protein coupled receptors.

Gpa2/Gpa1 Chimera Used to Attempt to Couple Gpa2 to Ste2

Previous studies in mammalian yeast systems have suggested that the expression of chimeric G-protein α-subunits can be a means to couple different G-protein coupled receptors to the same signaling pathway (Kajkowski, E. M., et al., *J. Receptor Signal Transduction Res.* 17:293–303 (1997); Kang, Y. S., et al., *Mol. Cell. Biol.* 10:2582–2590 (1990); Osawa, S., et al., *Cell* 63:697–706 (1990); Price, L. A., et al., *Mol. Cell. Riol.* 15:6188–6195 (1995)). In general, experimental evidence suggests that the carboxy-terminal domain of G-protein α-subunits is involved in receptor binding, the amino-terminal portion of the molecule functions to bind β-subunits, and the sequence near the carboxy-terminus promotes effector interactions (Conklin, B. R., et al., *Cell* 73:631–641 (1993); Watson, S., et al., "*The G-Protein Linked Receptor Factsbook*", Academic Press Limited, London (1994)).

G-protein α-subunits can be engineered to contain a carboxy-terminus that targets a specific class of receptors and amino-terminus that activates a specific signaling pathway. Thus, construction of a $NH_2$-Gpa2-Gpa1-COOH chimera could facilitate the coupling of Ste2 to the Gpa2-dependent cAMP response.

A Gpa2/Gpa1 chimeric α-subunit was constructed by introducing a silent mutation into the coding sequence for a residue in the Gpa2 GTP-binding pocket. This silent mutation created a BamHI site that was used for cloning the carboxy-terminal portion of Gpa1 in frame with GPA2 coding sequence. The resulting construct encodes a chimeric 450 amino acid protein ($NH_2$-307 amino acid Gpa2-143 amino acid Gpa1-COOH). The chimeric protein is expressed under the control of the GPA2 promoter. The Gpa2/Gpa1 clone was then introduced into a diploid gpa2 strain (MMB1205) containing PGK-STE2 in order to determine whether addition of a factor would trigger the yeast cAMP response.

A homozygous diploid gpa2Δ::URA3/gpa2Δ::URA3 strain containing PGK-STE2 was transformed with low-copy plasmids expressing either Gpa2, Gpa2 Q>300L, Gpa2/Gpa1 or an empty pRS415 vector (to produce strains MMB1206, MMB1207, MMB1205, and MMB1210 listed in FIG. 2). Pseudohyphal growth assays were performed on SLAD plates either containing or lacking α factor. As described above, gpa2 strains (MMB1210) fail to form pronounced filaments, whereas strains expressing Gpa2 Q>300L undergo more exaggerated pseudohyphal growth than wild-type strains. Strains expressing the Gpa2/Gpa1 chimeric protein displayed similar levels of pseudohyphal growth both in the presence and absence of several concentrations of α factor (approximately 0.03, 0.33, and 3.33 μg/ml final concentration). The degree of filament formation observed in transformed yeast strains expressing Gpa2/Gpa1 was only slightly lower than that observed in strains expressing wild-type Gpa2. Thus, the Gpa2/Gpa1 chimeric protein can partially complement the gpa2 filament formation defect in a ligand-independent manner. Similar results were detected when glycogen accumulation assays were performed on gpa2 strains expressing the Gpa2/Gpa1 chimeric protein both in the presence and absence of a factor. Together these experiments suggested that the chimeric protein is expressed and functional; however, the Gpa2/Gpa1 chimeric protein cannot facilitate coupling to the Ste2 G-protein coupled receptor. Alternatively, these phenotypic assays may not have been sufficiently sensitive to detect a low level of coupling events.

Transcriptional profiling provides a means to detect genome-wide changes in expression patterns. In an effort to detect subtle changes in expression that may suggest coupling of the chimeric Gpa2/Gpa1 protein to the Ste2 G-protein coupled receptor, transcriptional profiling was performed on nylon microarrays of 6000 yeast predicted open reading frames (ORFs). Each ORF was spotted twice on the microarray in an effort to ensure reproducibility in the data. Early log phase cultures ($OD_{600}$=0.2) of diploid gpa2 strains expressing GPA2/GPA1 and either PGK-STE2

(MMB1205) or empty YPGE2 (MMB1209) vector were treated with α factor (3 μg/ml) for 3 or 6 hours, cells harvested, and RNA prepared for transcriptional profiling. RNA was also prepared from diploid Gpa2 strains containing either the low-copy pRS415 vector (MMB1210), low-copy GPA2 (MMB1206), or low copy GPA2 Q300>L (MMB1207). These strains were grown in the same media and to the same growth stage as described above. Normalized values for each profiling experiment were calculated as described in detail in the Exemplification and relevant ratios were calculated. An analysis of the ratio of low copy GPA2 Q300>L normalized values to low-copy GPA2 values produced subsets of genes displaying either Gpa2-dependent induction or repression of expression. Successful coupling of the Gpa2/Gpa1 chimeric α-subunit to the Ste2 G-protein coupled receptor should, in response to α factor, alter PGK-STE2 to either induce or repress the expression of similar subsets of genes as activated Gpa2. Furthermore, the subsets of genes regulated by the presence of PGK-STE2 may be conserved at both the 3 hour and 6 hour timepoints. However, neither of these results were observed. Together with the phenotypic analyses described above, these data suggest that in this experimental design the Gpa2/Gpa1 chimeric subunit is not sufficient to promote coupling to the Ste2 G-protein coupled receptor.

The relative expression levels of the G-protein coupled receptor and G-protein α-subunit is one variable that could be experimentally manipulated in an attempt to establish a functional system using chimeric G-protein α-subunits.

The GPA2 promoter was used to express the GPA2/GPA1 chimeric transcript from a low-copy plasmid, whereas STE2 was expressed from the PGK promoter present on a high-copy plasmid. Transcriptional profiling revealed that STE2 expression was approximately sixty-four fold higher than GPA2/GPA1 (FIG. 3). The Ste2-Gpa2 chimeric protein was expressed at a much lower level than the Gpa2/Gpa1 fusion protein. The expression of actin (ACT1) did not significantly change (FIG. 3). Previous studies in the Gpa1 system for studying G-protein coupled receptors in yeast have demonstrated that high levels of G-protein α-subunit expression can be detrimental (Kang, Y.-S., et al., *Mol. Cell. Biol.* 10:2582–2590 (1990); Price, L. A., et al., *Mol. Cell. Biol.* 15:6188–6195 (1995)). It has been suggested that a pool of free G-protein α-subunits can sequester βγ- subunits or effectors, such that ligand-dependent activation can not be detected. Regardless, the ratio of STE2 to GPA2/GPA1 expression is dramatic enough that it may be beneficial to explore whether increased expression of the chimera is sufficient to promote coupling.

Transcriptional profiling studies determined that STE2 was expressed from the PGK promoter at approximately 36 to 135 fold higher levels than the GPA2/GPA1 construct was being expressed from the GPA2 promoter. As described above, increased expression of the chimeric protein can allow for coupling to the Ste2 receptor. Coding sequence for the Gpa2/Gpa1 chimera protein can be cloned into plasmids to be expressed under the regulation of both the PGK and GAL promoters. The GAL-GPA2/GPA1 construct can be used to express increasing amounts of chimeric protein as the concentration of glucose in the medium is decreased.

G-Protein Coupled Receptor and G-Protein αSubunit Fusion Proteins Activate Signaling in a Ligand Dependent Manner To determine whether covalent fusion of Ste2 to Gpa2 activates the yeast cAMP response in an a factor dependent manner, the complete coding sequence of GPA2 was cloned into PGK-STE2 in frame with STE2. The GPA2/GPA1 construct coding sequence was also cloned into the same site. The resulting fusion proteins are expected to lack the coding sequence for the final 62 amino acids of Ste2. A similar Ste2-Gpa1 fusion protein has previously been shown to be functional (e.g., activates the mating response pathway upon pheromone treatment) (Medici, R., et al., *EMBO J.* 16:241–249 (1997)). Therefore, diploid strains expressing PGK-STE2-GPA2 and PGK-STE2-GPA2/GPA1 constructs were examine for activation of the cAMP response in the presence of a factor.

Transcriptional profiling was used to determine whether α factor treatment of strains containing PGK-STE2-GPA2 and PGK-STE2-GPA2/GPA1 constructs resulted in expression changes (e.g., transcriptional profiling) indicative of activation the yeast cAMP response. Cultures of diploid Gpa2 strains containing either PGK-STE2 (MMB1210), PGK-STE2-GPA2 (MMB1211), PGK-STE2-GPA2/GPA1 (MMB1212), or PGK-STE2+low copy GPA2 Q300>L (MMB1207) were grown to early log phase. Cultures samples were then split and either treated or not treated with α factor (9 μg/ml final concentration) for 3 hours. Cells were then harvested, RNA was prepared, and transcriptional profiling performed.

The following ratios were then calculated to compare profiles:

(A) PGK-STE2-GPA2+α factor/PGK-STE2-GPA2
(B) GPA2 Q300>L+α factor/GPA2 Q300>L
(C) GPA2 Q300>L+α factor/PGK-STE2-GPA2
(D) PGK-STE2-GPA2/GPA1+α factor/PGK-STE2-GPA2
(E) PGK-STE2-GPA2+α factor/PGK-STE2+α factor
(F) GPA2 Q300>L/PGK-STE2-GPA2
(G) GPA2 Q300>L+α factor/PGK-STE2+α factor
(H) GPA2 Q300>L+α factor/PGK-STE2-GPA2 +α factor
(I) PGK-STE2+α factor/PGK-STE2-GPA2

If α factor treatment of STE-GPA2 strains and an activated allele of GPA2 elicit similar cellular responses, then several ratios should correlate. The ratios A, C, E, F, and G should identify similar subsets of genes that are induced or repressed, whereas ratios B and I should not correlate with transcription profiles of A, C, E, F and G. Ratio D should correlate with transcriptional profiling of A, C, E, F and G if the Gpa2/Gpa1 chimera is competent for signaling. Ratio H can provide insight into the level of activation of the cAMP-dependent response by PGK-STE2-GPA2. Data were analyzed to determine subsets of genes for which both data points display either induction or repression >2.5 fold in each of the ratios A, C, D, E, F, and G (slight variance in one or few data points would not cause exclusion from further study). Genes that were also induced or repressed >2.5 fold in either B or I were excluded from further analysis. Ratio B is used to eliminate sets of genes that are regulated by the addition of a factor in a Gpa2-independent manner. Ratio I functions to both detect genes whose induction or repression is not regulated by Gpa2 as well as to possibly identify artifacts in the PGK-STE2-GPA2 (no α factor) data set. FIG. 4 depicts the transcriptional profiling data from a set of genes which are repressed by GPA2 activation.

Expression of several genes appears to be regulated both by ligand binding to the Ste2-Gpa2 fusion protein and an activated form of Gpa2. In addition, similar expression patterns are detected for strains expressing Ste2-Gpa2 and Ste2-Gpa2/Gpa1.

The observation that expression of similar subsets of genes is regulated both by ligand binding to the Ste2-Gpa2 fusion protein as well as by an activated form of Gpa2 is strong evidence that the use of heterologous G-protein coupled receptor G-protein α-subunit fusion proteins is a productive strategy for designing systems to study heterologous G-protein coupled receptors in yeast.

Additional evidence for the feasibility of using Gpa2 in such a system is that genes expected to be regulated by the cAMP-dependent response also are regulated by addition of pheromone to strains expressing the Ste2-Gpa2 fusion protein. Recent evidence has demonstrated that cAMP negatively regulates expression of genes containing upstream regulatory sequences known as stress response element(s) (STREs) (Gorner, W., et al., *Genes & Dev.* 12:586–597 (1998); Marchler, G., et al., *EMBO J.* 12:1997–2003 (1993); Varela, J. C., et al., *A. Mol. Cell. Biol.* 15:6232–6245 (1995)). Under stress conditions, including heat-shock, carbon-source starvation, and low nitrogen, the Msn2 and Msn4 transcription factors bind STREs and activate transcription (Gorner, W., et al., *Genes & Dev.* 12:586–597 (1998); Boy-Marcotte, E., et al., *J. Bacteriol.* 180:1044–1052 (1998); Crauwels, M., et al., *Microbiology* 143:2627–2737 (1997); Martinez-Pastor, M. T., et al., *EMBO J.* 15:2227–2235 (1996); Schmitt, A. P., et al., *Proc. Natl. Acad. Sci.* 93:5777–5782 (1996); Flattery-O'Brien, J. A., et al., *Mol. Microbiol.* 23:303–312 (1997)). High levels of cAMP drive the nuclear to cytoplasmic translocation of Msn2 (Gorner, W., et al., *Genes & Dev.* 12:586–597 (1998)). Thus, high levels of cAMP are expected to decrease the expression level of genes containing STREs. A preliminary analysis was performed on upstream regulatory sequence (750 basepairs from the ATG) of twenty two genes that were identified as repressed by GPA2 activation (FIGS. 5 and 6). The 750 base pairs of upstream regulatory sequence were searched for exact matches to the core (5'-CCCCT-3' or complimentary 5'-AGGGG-3') STRE predicted binding site.

The core sequence for a STRE is 5'-CCCCT-3' (Ruis, H., et al., *BioEssays* 17:959–965 (1995); Siderius, M., et al., "Yeast Stress Responses" pages 213–230, Hohmann, S., et al., (eds.), Landes, Austin, Tex. (1997)). Fifteen of the twenty two promoters analyzed contained at least one precise STRE core element (FIG. 6). These data show that ligand binding to Ste2-Gpa2 represses expression of genes containing upstream regulatory elements that are known to be negatively regulated by cAMP.

In addition, the observation that regulatory sequences of multiple genes that are repressed by Gpa2 activation contain predicted STREs suggest that transcriptional profiling experiments performed in conditions which are known to activate expression of genes that contain STREs can help identify additional repressed genes and possibly promoters of other genes which can be induced under these conditions. Transcriptional profiling experiments performed in low nitrogen medium (known to activate expression of genes containing STREs) indicates that expression of HSP12, HSP26, YNL134C and YML128c increases significantly in low nitrogen media relative to rich medium (FIG. 5). Activation of Gpa2 represses the expression of these genes. Further analysis can identify gene(s) whose expression is induced by activation of Gpa2 under conditions of stress.

Ras2 signaling also regulates the yeast cAMP response. Glycogen accumulation assays suggest that Ras2 functions as the major regulator of cAMP production (Kübler, E., et al., *J. Biol. Chem.* 272:20321–20323 (1997)). Therefore, a strain that is compromised for Ras2 signaling can be a very sensitive strain for monitoring activation of Gpa2. Experiments can be performed to address transcriptional changes elicited by addition of ligand to ras2Δ strains that express Ste2-Gpa2. Transcriptional profiling experiments described herein were performed in a gpa2Δ strain; ras2Δ gpa2Δ strains, can also be useful. However ras2Δ gpa2Δ strains have severe growth defects; it is possible that ras2Δ gpa2Δ strains can be maintained by addition of exogenous cAMP or cAMP analogues to the growth medium. Addition of ligand to a ras2Δ gpa2Δ strain comprising a fusion protein described herein that has been transferred to media lacking cAMP may elicit a very pronounced cAMP response. Alternatively a ras2Δ strain can be a more sensitive background for monitoring Gpa2 activation than a gpa2Δ strain.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A transformed yeast cell responsive to G-protein coupled activation of a yeast Gα Gpa2 protein comprising a nucleic acid construct comprising a promoter selected from the group consisting of YMR323w, YBL100c, YDR187c, YEL045c, YBLO96c, YNL028w, YFR056c, PHO4, YCL046w, YPL281c, YJL045w, YGL046w, GLK1, YML058c-a, YJR114w, IDH2, YML035c-a, HSP12, HSP26, YNL134c and YML128c, wherein said promoter is operably linked to a heterologous first DNA sequence which is operably linked to a second DNA sequence, wherein said heterologous first DNA sequence encodes a mammalian G-protein coupled receptor, and wherein said second DNA sequence encodes a yeast Gα Gpa2 protein, such that expression of the first and second DNA sequences produces a fusion protein wherein the yeast Gα Gpa2 protein is linked to the mammalian G-protein coupled receptor, and wherein binding of a ligand to the mammalian G-protein coupled receptor results in alteration of cellular levels or activity of adenylate cyclase and/or cAMP.

2. A transformed yeast cell according to claim 1, wherein the promoter is a constitutive promoter.

3. A transformed yeast cell according to claim 1, wherein the endogenous gene encoding Gpa2 comprises a loss of function mutation.

4. A transformed yeast cell according to claim 1, further comprising a Gpa2-responsive promoter operably linked to a third DNA sequence encoding a reporter gene.

5. A transformed yeast cell according to claim 4, wherein the Gpa2-responsive promoter is a promoter of a gene selected from the group consisting of YMR323w, YBL100c, YDR187c, YEL045c, YBLO96c, YNL028w, YFR056c, PHO4, YCL046w, YCLX09w, YPL281c, YJL045w, YGL046w, GLK1, YML058c-a, YJR114w, IDH2, YML035c-a, HSP12, HSP26, YNL134c and YML128c.

6. A transformed yeast cell according to claim 4, wherein the reporter gene is selected from the group consisting of enzymes, luminescent molecules and auxotrophic markers.

7. A transformed yeast cell according to claim 4, wherein the reporter gene is an enzyme and is selected from the group consisting of β-galactosidase, β-glucoronidase, β-glucosidase, acid phosphatase, and invertase.

8. A transformed yeast cell according to claim 4, wherein the reporter gene is a luminescent molecule and is selected from the group consisting of green fluorescent protein and firefly luciferase.

9. A transformed yeast cell according to claim 6, wherein the reporter gene is an auxotrophic marker and is selected from the group consisting of HIS3, URA3 and LYS2.

10. A nucleic acid construct comprising a promoter selected from the group consisting of YMR323w, YBL100c, YDR187c, YEL045c, YBLO96c, YNL028w, YFR056c, PHO4, YCL046w, YPL281c, YJL045w, YGL046w, GLK1, YML058c-a, YJR114w, IDH2, YML035c-a, HSP12, HSP26, YNL134c and YML128c, wherein said promoter is operably linked to a heterologous first DNA sequence which is operably linked to a second DNA sequence, wherein said heterologous first DNA sequence encodes a mammalian G-protein coupled receptor, and wherein said second DNA sequence encodes a yeast Gα Gpa2 protein, such that expression of the first and second DNA sequences produces a fusion protein wherein the yeast Gα Gpa2 protein is linked to the mammalian G-protein coupled receptor.

11. A nucleic acid construct according to claim 10, wherein the promoter is a constitutive promoter.

12. A transformed yeast cell responsive to G-protein coupled activation of a yeast Gα Gpa2 protein comprising a nucleic acid construct comprising a promoter selected from the group consisting of YMR323w, YBL100c, YDR187c, YEL045c, YBLO96c, YNL028w, YFR056c, PHO4, YCL046w, YPL281c, YJL045w, YGL046w, GLK1, YML058c-a, YJR114w, IDH2, YML035c-a, HSP12, HSP26, YNL134c and YML128c, wherein said promoter is operably linked to a heterologous first DNA sequence which is operably linked to a second DNA sequence, wherein said heterologous first DNA sequence encodes a G-protein coupled receptor, and wherein said second DNA sequence encodes a yeast Gpa2 protein, such that expression of the first and second DNA sequences produces a fusion protein wherein the yeast Gpa2 protein is linked to the mammalian G protein coupled receptor.

* * * * *

UNITED STATES PATENT AND TRADEMARK OFFICE
CERTIFICATE OF CORRECTION

PATENT NO. : 6,280,934 B1  
DATED : August 28, 2001  
INVENTOR(S) : Kevin T. Madden, Patrick R. Errada and Carlos J. Gimeno It is certified that error appears in the above-identified patent and that said Letters Patent is hereby corrected as shown below:

Column 37,
Lines 53-59, delete claim 5.

Signed and Sealed this

Twenty-fifth Day of June, 2002

Attest:

JAMES E. ROGAN
Attesting Officer       Director of the United States Patent and Trademark Office

SEQUENCE LISTING

<160> NUMBER OF SEQ ID NOS: 30

<210> SEQ ID NO 1
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 1
acgcgtcgac gataggaaca atacgacaag gg                32

<210> SEQ ID NO 2
<211> LENGTH: 32
<212> TYPE: DNA
<213> ORGANISM: Artificial Sequence
<220> FEATURE:
<223> OTHER INFORMATION: Synthetic Oligonucleotide

```
<400> SEQUENCE: 2
cgcggatccc agagacccat gatatttgct tg                              32

<210> SEQ ID NO 3
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 3
cgcggatccg tgttacaatg aatgcacagc ta                              32

<210> SEQ ID NO 4
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 4
cctaggcgag ctctccgcat tcaaaagctc ctg                             33

<210> SEQ ID NO 5
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 5
acgcgtcgac acgggcgtgg ccgtatcaat g                               31

<210> SEQ ID NO 6
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 6
cgcggatcct ctgtatatct cctttcaat                                  29

<210> SEQ ID NO 7
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 7
cgcggatccg gctgttgtat tataagttaa                                 30

<210> SEQ ID NO 8
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 8
cctaggcgag ctcgattatc gtcctcaccg gcat                            34

<210> SEQ ID NO 9
```

<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 9
aaaactgcag cgggtaaccc gtggtacccg gggc             34

<210> SEQ ID NO 10
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 10
ctagtctaga attgtcgaag cagtggatcc atttt            35

<210> SEQ ID NO 11
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 11
cgcggatcca ctgcttcgac aatgtcac                    28

<210> SEQ ID NO 12
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 12
ctagtctaga tgttacccgg gataataact ata              33

<210> SEQ ID NO 13
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 13
tcaacttgac tgtgatgatc cgatc                       25

<210> SEQ ID NO 14
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 14
tccttcgaaa caatggatcc acttct                      26

<210> SEQ ID NO 15
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 15

```
agaagtggat ccattgtttc gaagga                                              26

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
tctgcatcgc cgacacgtcc                                                     20

<210> SEQ ID NO 17
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 17
tcaacttgac tgtgatgatc cgatc                                               25

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
tctgcatcgc cgacacgtcc                                                     20

<210> SEQ ID NO 19
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 19
acgtgggtgg actgcgttcc gaaag                                               25

<210> SEQ ID NO 20
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 20
ctttcggaac gcagtccacc cacgt                                               25

<210> SEQ ID NO 21
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 21
agcggatcca aaaaaatgtc tgatgcggct ccttc                                    35

<210> SEQ ID NO 22
<211> LENGTH: 36
<212> TYPE: DNA
```

```
<213> ORGANISM: Artificial Sequence
<220> FEATURE:
<223> OTHER INFORMATION: Synthetic Oligonucleotide

<400> SEQUENCE: 22
agcagtggcg cctgaatcta gtagtaacct tatacc                                  36

<210> SEQ ID NO 23
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 23
accgctgcag atggtctctg cgcatcttca gaa                                     33

<210> SEQ ID NO 24
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 24
ccgctcgagg tcgacgctgt gcattcattg taacactcc                               39

<210> SEQ ID NO 25
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 25
accgctgcag atggtctctg cgcatcttca gaa                                     33

<210> SEQ ID NO 26
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 26
ccgctcgagg tcgaccagtt ccttcatata atacca                                  36

<210> SEQ ID NO 27
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 27
cgtgtcgaca gatctaaaaa atggagatga gctctgag                                38

<210> SEQ ID NO 28
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 28
tcgctcgagg tcgactcaga tactggtttg gaggt                                   35
```

```
<210> SEQ ID NO 29
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 29
cgtgtcgaca gatctaaaaa atggagatga gctctgag                                38

<210> SEQ ID NO 30
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 30
ctccgctgca gcgatactgg tttggaggtc tcc                                     33
```